US012642205B2

(12) United States Patent
Vanoli et al.

(10) Patent No.: US 12,642,205 B2
(45) Date of Patent: Jun. 2, 2026

(54) LETTUCE VARIETY 'PIONEER'

(71) Applicant: Pinnacle Seed, Inc., Carmel, CA (US)

(72) Inventors: Mike Vanoli, Carmel, CA (US);
Michael Koda, Carmel, CA (US)

(73) Assignee: Pinnacle Seed, Inc., Carmel, CA (US)

( * ) Notice: Subject to any disclaimer, the term of this patent is extended or adjusted under 35 U.S.C. 154(b) by 183 days.

(21) Appl. No.: 18/462,294

(22) Filed: Sep. 6, 2023

(65) Prior Publication Data

US 2024/0090399 A1 Mar. 21, 2024

Related U.S. Application Data

(60) Provisional application No. 63/404,795, filed on Sep. 8, 2022.

(51) Int. Cl.
*A01H 6/14* (2018.01)
*A01H 5/12* (2018.01)

(52) U.S. Cl.
CPC ............. *A01H 6/1472* (2018.05); *A01H 5/12* (2013.01)

(58) Field of Classification Search
None
See application file for complete search history.

(56) References Cited

U.S. PATENT DOCUMENTS

| | | | |
|---|---|---|---|
| 7,371,933 B1 | 5/2008 | Knerr | |
| 8,362,326 B2 | 1/2013 | Bellec | |
| 8,389,810 B2 | 3/2013 | Ammerlaan | |
| 8,404,937 B2 | 3/2013 | Gibson | |
| 8,476,498 B2 | 7/2013 | Peng | |
| 8,772,578 B2 | 7/2014 | Ammerlaan | |
| 8,835,719 B2 | 9/2014 | Gibson | |
| 9,320,250 B2 | 4/2016 | Ammerlaan | |
| 9,706,743 B2 | 7/2017 | Heintzberger et al. | |
| 9,814,210 B2 | 11/2017 | Ammerlaan et al. | |
| 9,913,452 B2 | 3/2018 | Munoz | |
| 10,123,502 B2 | 11/2018 | Vanoli | |
| 10,631,491 B2 | 4/2020 | Vanoli | |
| 10,785,937 B1 * | 9/2020 | Vanoli | A01H 6/1472 |
| 11,369,069 B2 | 6/2022 | Vanoli | |
| 11,369,070 B2 | 6/2022 | Vanoli et al. | |
| 11,723,329 B2 | 8/2023 | Vanoli et al. | |
| 11,758,861 B2 | 9/2023 | Vanoli | |
| 11,944,054 B2 | 4/2024 | Sinclair | |
| 12,207,608 B2 | 1/2025 | Vanoli | |
| 12,389,846 B2 | 8/2025 | Vanoli et al. | |
| 2012/0278955 A1 | 11/2012 | Gibson | |
| 2012/0297496 A1 | 11/2012 | van der Laan | |
| 2013/0171323 A1 | 7/2013 | Jansen et al. | |
| 2014/0101794 A1 | 4/2014 | Gibson | |
| 2015/0208602 A1 | 7/2015 | Waycott | |
| 2017/0251622 A1 | 9/2017 | Sinclair et al. | |
| 2018/0249669 A1 | 9/2018 | Sinclair | |
| 2019/0230883 A1 | 8/2019 | Heintzberger et al. | |
| 2020/0288660 A1 | 9/2020 | Vanoli | |
| 2020/0375137 A1 | 12/2020 | Vanoli | |
| 2021/0084853 A1 | 3/2021 | Vanoli | |
| 2022/0264814 A1 | 8/2022 | Vanoli et al. | |
| 2022/0279747 A1 | 9/2022 | Vanoli | |
| 2022/0346338 A1 | 11/2022 | Vanoli et al. | |
| 2023/0329174 A1 | 10/2023 | Vanoli et al. | |
| 2024/0040983 A1 | 2/2024 | Vanoli | |
| 2024/0090399 A1 | 3/2024 | Vanoli et al. | |
| 2025/0268167 A1 | 8/2025 | Vanoli et al. | |
| 2025/0287894 A1 | 9/2025 | Vanoli et al. | |

OTHER PUBLICATIONS

USDA, "Applying for a Plant Variety Certificate of Protection", https://www.ams.usda.gov/services/pvpo/application-help/apply, accessed May 1, 2023.*
UPOV, 2017, Explanatory Notes on Essentially Derived Varieties Under the 1991 Act of the UPOV Convention.*
Ex Parte C (USPQ 2d 1492 (1992).*
Ex Parte McGowen—Board Decision in U.S. Appl. No. 14/996,093. (Year: 2020).*
Huan et al. Plant Physiology. 155:645-655. (Year: 2011).*
Großinsky et al. Journal of Experimental Botany. 66(18):5429-5440. (Year: 2015).*
Grant, A. (2018). "Different Lettuce Types: Varieties of Lettuce for the Garden," Obtained from <https://www.gardeningknowhow.com/edible/vegetables/lettuce/different-lettuce-types.htm>, 7 pages.
Liu et al., (1999). "First Report of Tomato Bushy Stunt Virus Isolated from Lettuce," Plant Disease, 83(3):301, 3 pages.
Mikel, M. (2013). "Genetic composition of contemporary proprietary U.S. lettuce (*Lactuca sativa* L.) cultivars," Genet Resour Crop Evol, 60:89-96.
Nagata, R. T. (1992). "Clip and Wash Method of Emasculation for Lettuce." HortScience 27(8):907-908.
Notice of Release of iceberg lettuce breeding lines submitted by the United States Department of Agriculture and University of California, Davis dated Jun. 4, 2015 and Jul. 1, 2015, 4 pages.
Obermeier et al., (2001). "Characterization of Distinct Tombusviruses that Cause Diseases of Lettuce and Tomato in the Western United States." Phytopathology, 91(8): 797-806.
Pinnacle Seed. 2020. 'Latitude'. Product Fact Sheet. Available online at <https://pinnacleseed.com/wp-content/uploads/sites/14/2020/12/Pinnacle-Seed-Brochure_Iceberg-Latitude.pdf>, 1 page.
Pinnacle Seed. 2020. 'Pacific Heart'. Product Fact Sheet. Available online at <https://pinnacleseed.com/wp-content/uploads/sites/14/2020/12/Pinnacle-Seed-Brochure_Romaine_Pacific-Heart.pdf>, 1 page.
Pinnacle Seed. 2022. 'Coastal Icebergs'. Cheat Sheet. Distributed to growers on Dec. 1, 2022, 2 pages.
Pinnacle Seed. 2023. 'Desert'. Cheat Sheet. Distributed to growers on Jul. 19, 2023, 2 pages.

(Continued)

*Primary Examiner* — Mykola V. Kovalenko

*Assistant Examiner* — David R Byrnes

(74) *Attorney, Agent, or Firm* — Morrison & Foerster LLP

(57) ABSTRACT

New lettuce variety designated 'Pioneer' is described. 'Pioneer' exhibits stability and uniformity.

15 Claims, 23 Drawing Sheets
(23 of 23 Drawing Sheet(s) Filed in Color)

(56) References Cited

OTHER PUBLICATIONS

Pinnacle Seed. Jun. 2019. 'Hotshot'. Product Sell Sheet. Available online at <http://pinnacleseed.net/sell-sheets/hotshot-sell-sheet.pdf>, Obtained on Sep. 18, 2020.1 page.

Pinnacle Seed. Jun. 2019. 'Uppercut'. Product Sell Sheet. Available online at <http://pinnacleseed.net/sell-sheets/PIN-021-Uppercut-sell-sheet-R1-20200310.pdf>, Obtained on Sep. 18, 2020.1 page.

Pinnacle Seed. Oct. 2018. 'Dark Horse'. Product Sell Sheet. Available online at <http://pinnacleseed.net/sell-sheets/PIN-021-sell-sheets-dark-horse-R2-20200421.pdf>, Obtained on Sep. 18, 2020.1 page.

Ryder et al., (1974). "Mist depollination of lettuce flowers." HortScience, 9:584, 3 pages.

Ryder et al., (1998). "Crisphead Lettuce Resistant to Tipburn: Cultivar Tiber and Eight Breeding Lines," HortScience, 33(5):903-904.

US Plant Variety Protection Certificate No. 200700432, Issued Mar. 12, 2012, Variety Showtime, Crop Name Lettuce, Applicant Harris Moran Seed Company, 40 pages.

US Plant Variety Protection Certificate No. 201000303, Issued Jun. 19, 2013, Variety Caretaker, Crop Name Lettuce, Applicant Harris Moran Seed Company, 28 pages.

US Plant Variety Protection Certificate No. 201100043, Issued Mar. 21, 2018, Variety Thunderhead, Crop Name Lettuce, Applicant 3 Star Lettuce, LLC, 34 pages.

US Plant Variety Protection Certificate No. 8900281, Issued Jun. 30, 1992, Variety Raider, Crop Name Lettuce, Applicant Genecorp, Inc., 17 pages.

US Plant Variety Protection Certificate No. 9800023, Issued Nov. 26, 2020, Variety Headmaster, Crop Name Lettuce, Applicant Progeny Advanced Genetics, Inc., 35 pages.

Pinnacle Seed. 2024. 'Desert'. Cheat Sheet. Distributed to growers on Jun. 14, 2024, 2 pages.

US Plant Variety Protection Certificate No. 200200013, Issued Dec. 12, 2005, Variety Big Star, Crop Name Lettuce, Applicant Central Valley Seeds, Inc., 34 pages.

US Plant Variety Protection Certificate No. 200500262, Issued Feb. 5, 2008, Variety Bergam's Green, Crop Name Lettuce, Applicant Enza Zaden Beheer B.V., 54 pages.

Unpublished U.S. Appl. No. 19/058,615, filed Feb. 20, 2025, titled "Lettuce Variety 'PS 1541'." (Copy not submitted herewith pursuant to the waiver of 37 C.F.R. § 1.98(a)(2)(iii).

Unpublished U.S. Appl. No. 19/075,005, filed Mar. 10, 2025, titled "Romaine-Iceberg Lettuce Variety 'PS 2004'." (Copy not submitted herewith pursuant to the waiver of 37 C.F.R. § 1.98(a)(2)(iii)).

US Plant Variety Protection Certificate No. 200800308, Issued Mar. 12, 2012, Variety Black Belt, Crop Name Lettuce, Applicant Nunhems BV, 45 pages.

US Plant Variety Protection Certificate No. 200800037, Issued Jan. 22, 2009, Variety Estival, Crop Name Lettuce, Applicant Agriculture and Agri-Food Canada, 19 pages.

Unpublished U.S. Appl. No. 19/313,159, filed Aug. 28, 2025, titled "Lettuce Varieties 'PS 1530' and 'PS 1531'." (Copy not submitted herewith pursuant to the waiver of 37 C.F.R. § 1.98(a)(2)(iii)).

* cited by examiner

'Crusader'

'Hotshot'

'Big Shot'

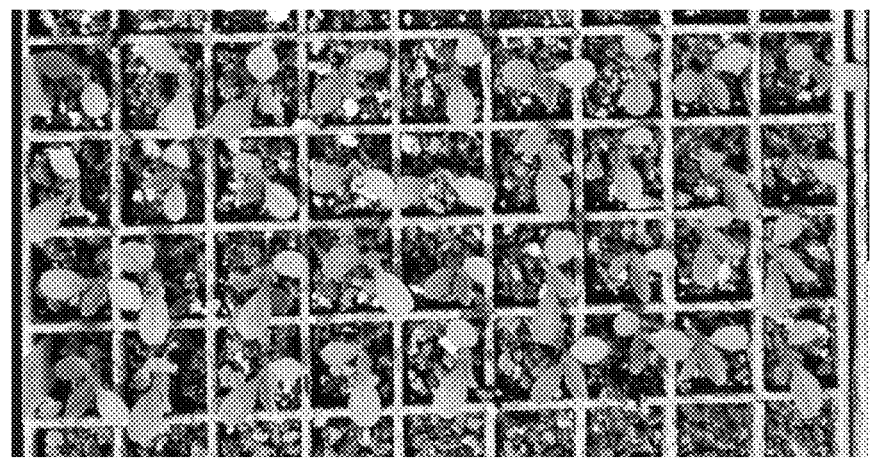
'Crusader'
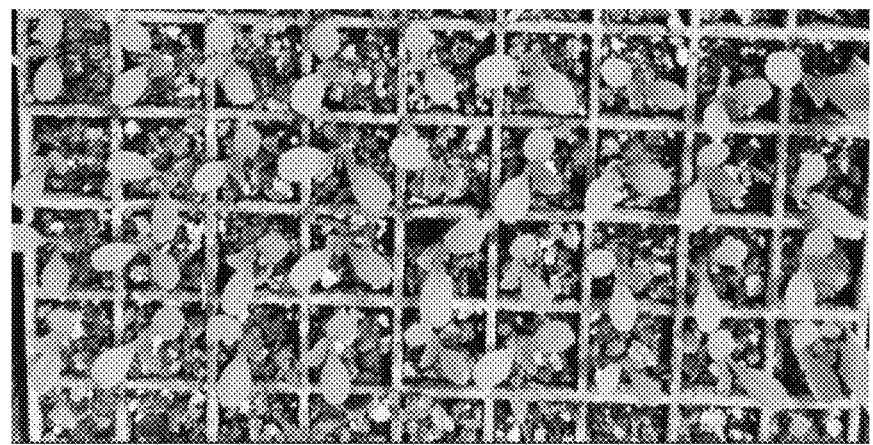
'Hotshot'
'Big Shot'
FIG. 1L

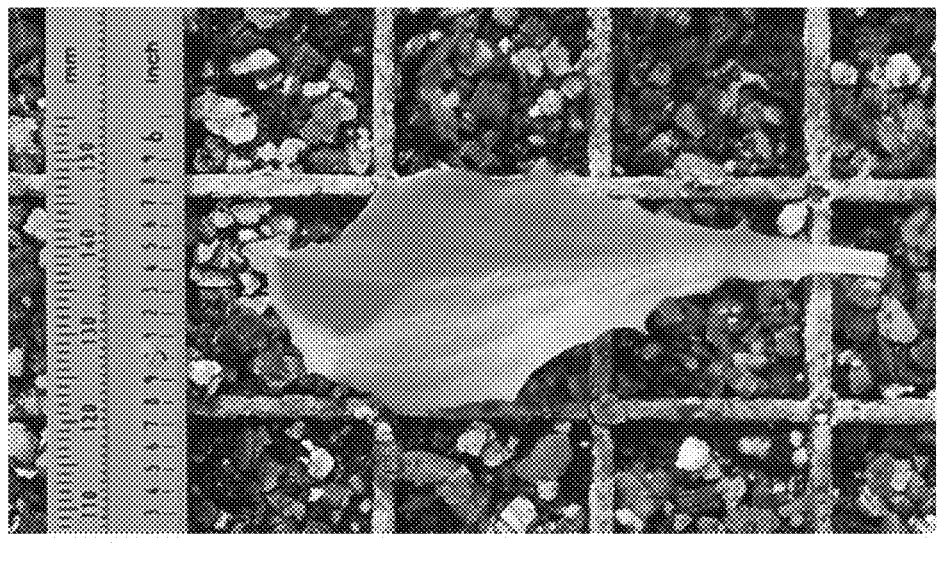
'Crusader'
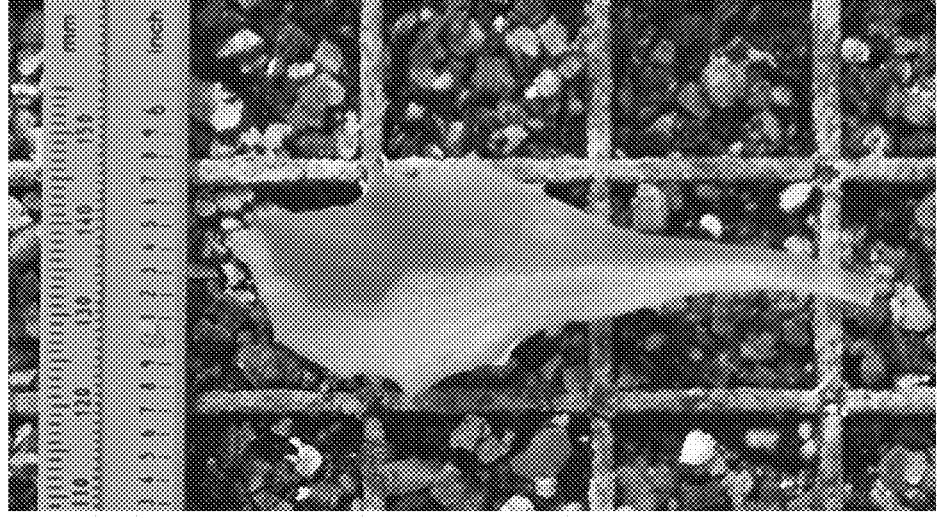
'Hotshot'
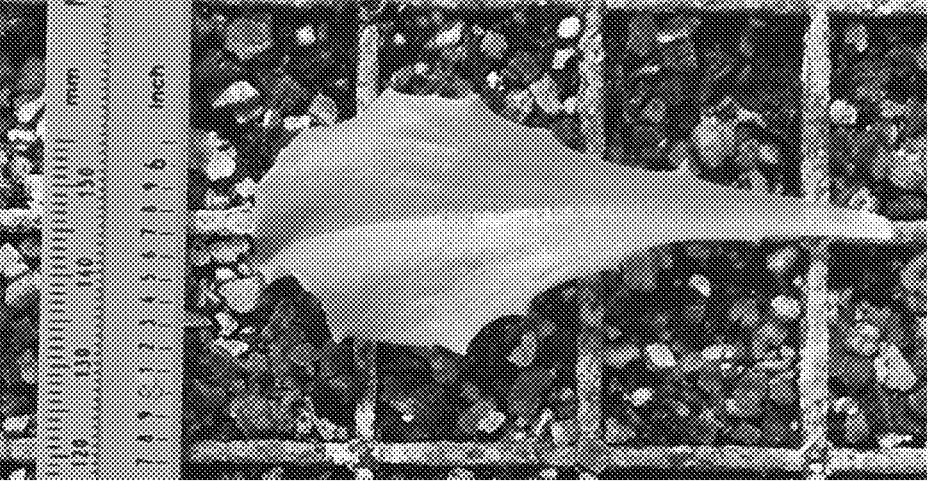
'Big Shot'
FIG. 1M

'Haymaker'
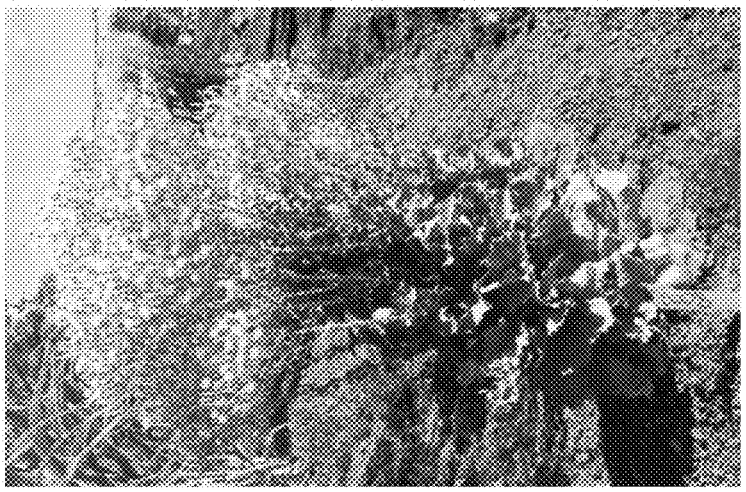
'Hercules'
'Pioneer'
FIG. 2K

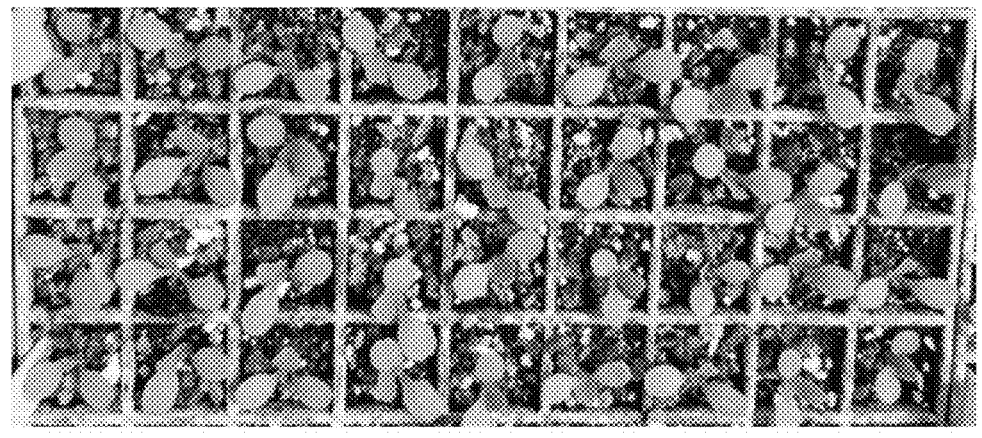
'Haymaker'
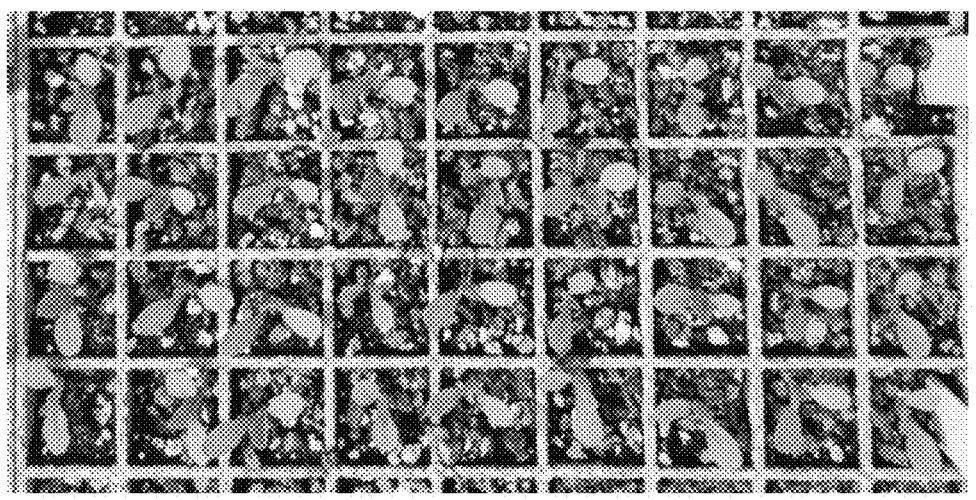
'Hercules'
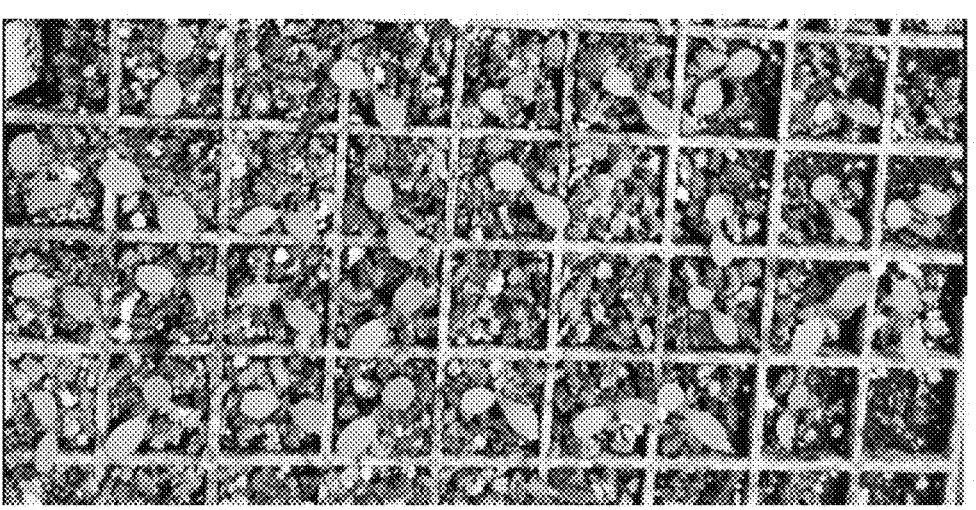
'Pioneer'
FIG. 2L

'Pioneer'      'Hercules'      'Haymaker'

LETTUCE VARIETY 'PIONEER'

CROSS-REFERENCE TO RELATED APPLICATION

This application claims the benefit of U.S. Provisional Application No. 63/404,795, filed Sep. 8, 2022, which is hereby incorporated by reference in its entirety.

FIELD

This invention relates to the field of plant breeding. In particular, this invention relates to new lettuce, *Lactuca sativa*, varieties 'Big Shot' and 'Pioneer'.

BACKGROUND

Lettuce is an increasingly popular crop. Worldwide lettuce consumption continues to increase. As a result of this demand, there is a continued need for new lettuce varieties. In particular, there is a need for improved lettuce varieties that are stable, high yielding, and agronomically sound.

SUMMARY

In order to meet these needs, the present invention is directed to improved lettuce varieties.

As used herein lettuce variety 'Pioneer' is the same lettuce variety as lettuce variety 'PS 1534' having ATCC Accession Number PTA-127991 and disclosed in U.S. Provisional Application No. 63/404,795. While the name has changed, lettuce variety 'Pioneer' has all the defining characteristics of lettuce variety 'PS 1534'.

In one embodiment, the present invention is directed to lettuce, *Lactuca sativa*, seed designated as 'Big Shot'. In one embodiment, the present invention is directed to a *Lactuca sativa* lettuce plant and parts isolated therefrom produced by growing 'Big Shot' lettuce seed. In another embodiment, the present invention is directed to a *Lactuca sativa* plant and parts isolated therefrom having all the physiological and morphological characteristics of a *Lactuca sativa* plant produced by growing 'Big Shot' lettuce seed. In still another embodiment, the present invention is directed to an $F_1$ hybrid *Lactuca sativa* lettuce seed, plants grown from the seed, and a head isolated therefrom having 'Big Shot' as a parent, where 'Big Shot' is grown from 'Big Shot' lettuce seed.

Lettuce plant parts include lettuce heads, lettuce leaves, parts of lettuce leaves, pollen, ovules, flowers, and the like. In another embodiment, the present invention is further directed to lettuce heads, lettuce leaves, parts of lettuce leaves, flowers, pollen, and ovules isolated from 'Big Shot' lettuce plants. In another embodiment, the present invention is further directed to tissue culture of 'Big Shot' lettuce plants, and to lettuce plants regenerated from the tissue culture, where the plant has all of the morphological and physiological characteristics of 'Big Shot' lettuce plants.

The present invention is further directed to a method of selecting lettuce plants by: a) growing more than one 'Big Shot' lettuce plant, where the plants are grown from lettuce seed; and b) selecting a plant from step a). The present invention is further directed to lettuce plants and seeds produced therefrom, where the lettuce plants and seeds are isolated by the selection method of the invention.

In another embodiment, the present invention is further directed to a method of breeding lettuce plants by crossing a lettuce plant with a plant grown from 'Big Shot' lettuce seed. In still another embodiment, the present invention is further directed to lettuce plants, lettuce parts from the lettuce plants (e.g., lettuce heads), and seeds produced therefrom where the lettuce plant is isolated by the breeding method of the invention.

In one embodiment, the present invention is directed to lettuce, *Lactuca sativa*, seed designated as 'Pioneer' having ATCC Accession Number PTA-127991. In one embodiment, the present invention is directed to a *Lactuca sativa* lettuce plant and parts isolated therefrom produced by growing 'Pioneer' lettuce seed. In another embodiment, the present invention is directed to a *Lactuca sativa* plant and parts isolated therefrom having all the physiological and morphological characteristics of a *Lactuca sativa* plant produced by growing 'Pioneer' lettuce seed having ATCC Accession Number PTA-127991. In still another embodiment, the present invention is directed to an $F_1$ hybrid *Lactuca sativa* lettuce seed, plants grown from the seed, and a head isolated therefrom having 'Pioneer' as a parent, where 'Pioneer' is grown from 'Pioneer' lettuce seed having ATCC Accession Number PTA-127991.

Lettuce plant parts include lettuce heads, lettuce leaves, parts of lettuce leaves, pollen, ovules, flowers, and the like. In another embodiment, the present invention is further directed to lettuce heads, lettuce leaves, parts of lettuce leaves, flowers, pollen, and ovules isolated from 'Pioneer' lettuce plants. In another embodiment, the present invention is further directed to tissue culture of 'Pioneer' lettuce plants, and to lettuce plants regenerated from the tissue culture, where the plant has all of the morphological and physiological characteristics of 'Pioneer' lettuce plants.

The present invention is further directed to a method of selecting lettuce plants by: a) growing more than one 'Pioneer' lettuce plant, where the plants are grown from lettuce seed having ATCC Accession Number PTA-127991; and b) selecting a plant from step a). The present invention is further directed to lettuce plants and seeds produced therefrom, where the lettuce plants and seeds are isolated by the selection method of the invention.

In another embodiment, the present invention is further directed to a method of breeding lettuce plants by crossing a lettuce plant with a plant grown from 'Pioneer' lettuce seed having ATCC Accession Number PTA-127991. In still another embodiment, the present invention is further directed to lettuce plants, lettuce parts from the lettuce plants (e.g., lettuce heads), and seeds produced therefrom where the lettuce plant is isolated by the breeding method of the invention.

BRIEF DESCRIPTION OF THE DRAWINGS

The patent or application file contains at least one drawing executed in color. Copies of this patent or patent application publication with color drawings will be provided by the office upon request and payment of the necessary fee.

FIGS. 1A-1M show comparisons between lettuce varieties 'Big Shot', 'Hotshot' (U.S. Pat. No. 11,369,070), and 'Crusader' (PVP Certificate No. 9800351). FIG. 1A shows a top view of heads of lettuce varieties 'Big Shot' (left) and 'Hotshot' (right). FIG. 1B shows a top view of heads of lettuce varieties 'Big Shot' (left) and 'Crusader' (right). FIG. 1C shows a bottom view of heads of lettuce varieties 'Big Shot' (left) and 'Hotshot' (right). FIG. 1D shows a bottom view of heads of lettuce varieties 'Big Shot' (left) and 'Crusader' (right). FIG. 1E shows a side view of heads of lettuce varieties 'Big Shot' (left) and 'Hotshot' (right). FIG. 1F shows a side view of heads of lettuce varieties 'Big Shot'

3

Figure 1A:
Figure 1B:
Figure 1C:
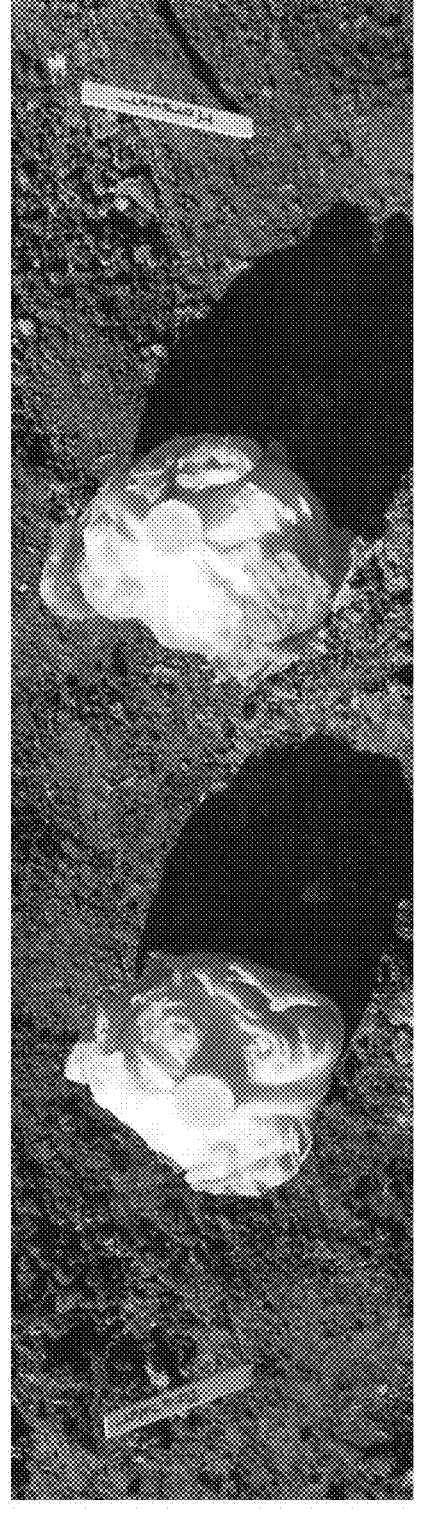
Figure 1D:
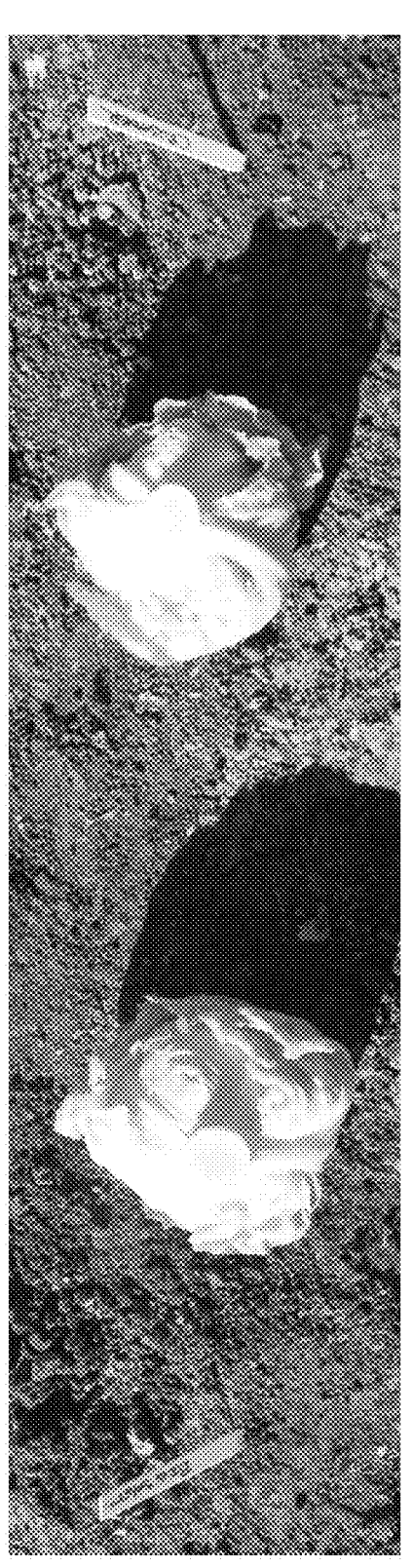
Figure 1E:
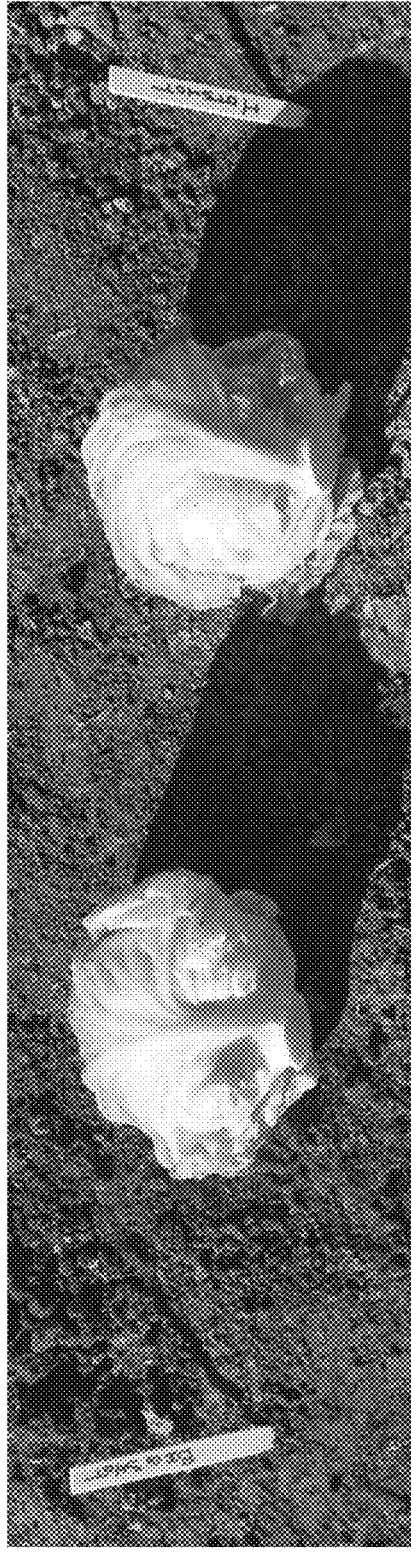
Figure 1F:
Figure 1G:
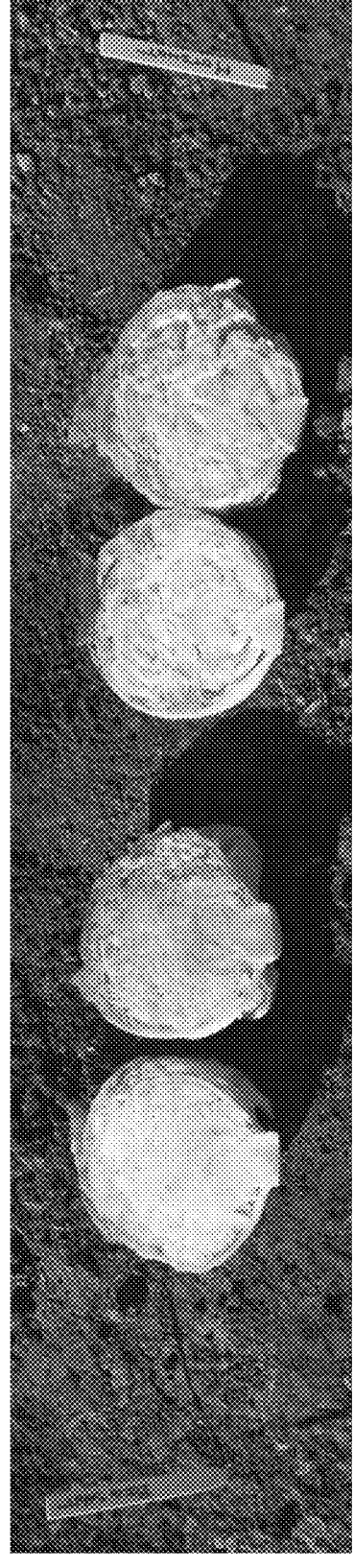
Figure 1H:
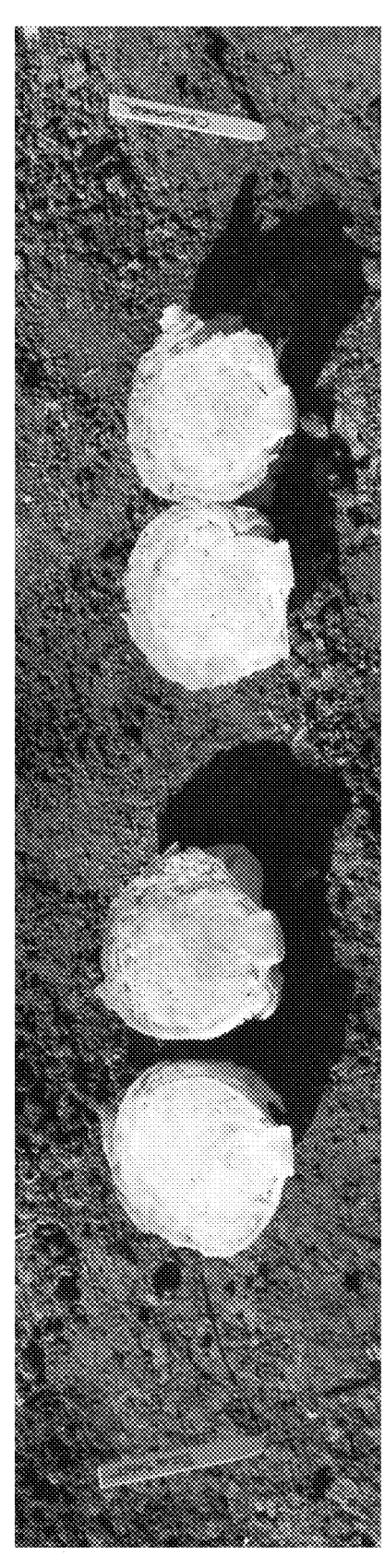
Figure 11:
Figure 1J:
Figure 1K:
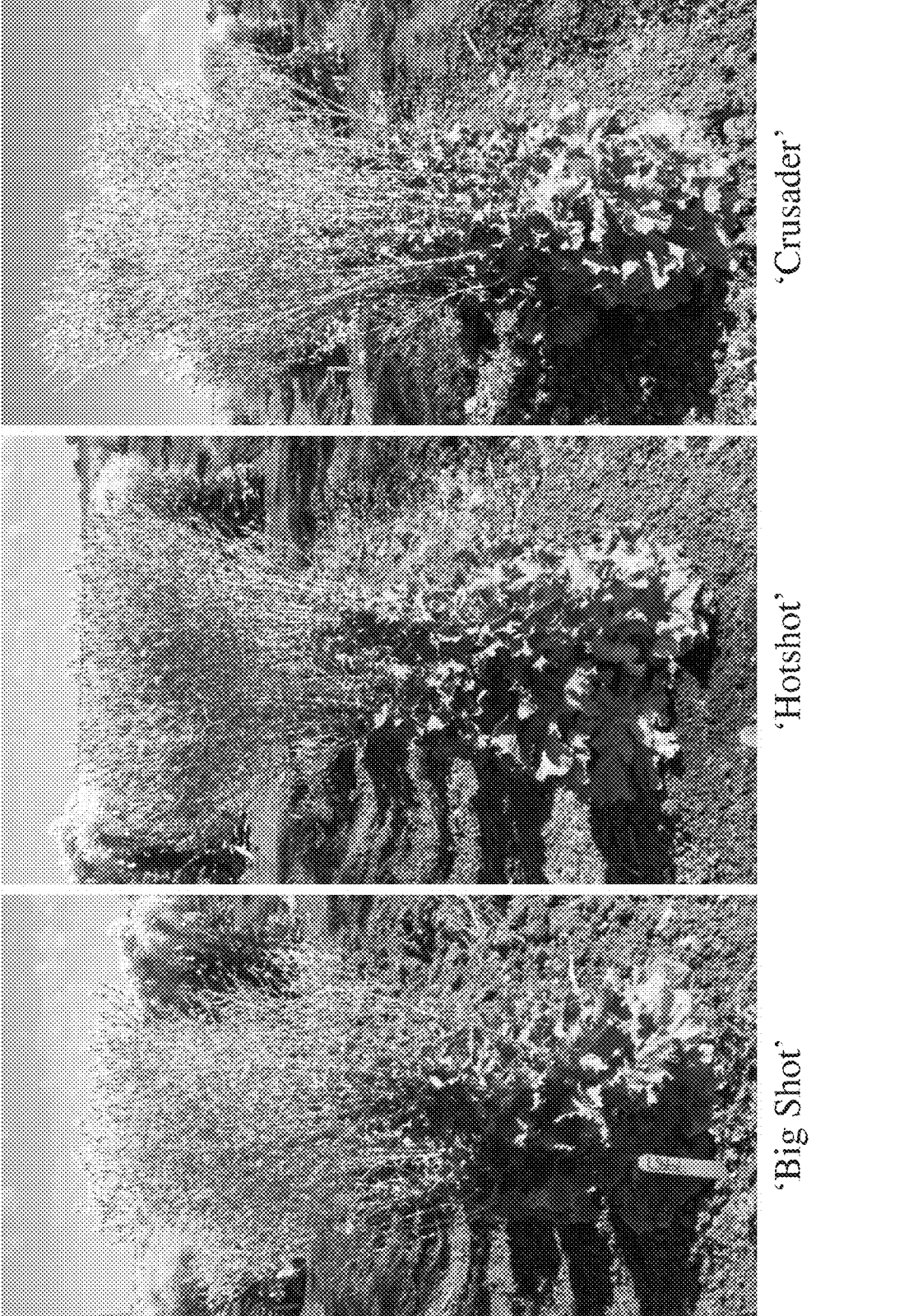

(left) and 'Crusader' (right). FIG. 1G shows a cross-sectional view of heads of lettuce varieties 'Big Shot' (left) and 'Hotshot' (right). FIG. 1H shows a cross-sectional view of heads of lettuce varieties 'Big Shot' (left) and 'Crusader' (right). FIG. 1I shows mature leaves of lettuce varieties 'Big Shot' (left) and 'Hotshot' (right). FIG. 1J shows mature leaves of lettuce varieties 'Big Shot' (left) and 'Crusader' (right). FIG. 1K shows plants, including stalks, of lettuce varieties 'Big Shot' (left), 'Hotshot' (center), and 'Crusader' (right) after bolting. FIG. 1L shows seedlings of lettuce varieties 'Big Shot' (left), 'Hotshot' (center), and 'Crusader' (right). FIG. 1M shows fourth leaves of lettuce varieties 'Big Shot' (left), 'Hotshot' (center), and 'Crusader' (right).

Figure 2A:
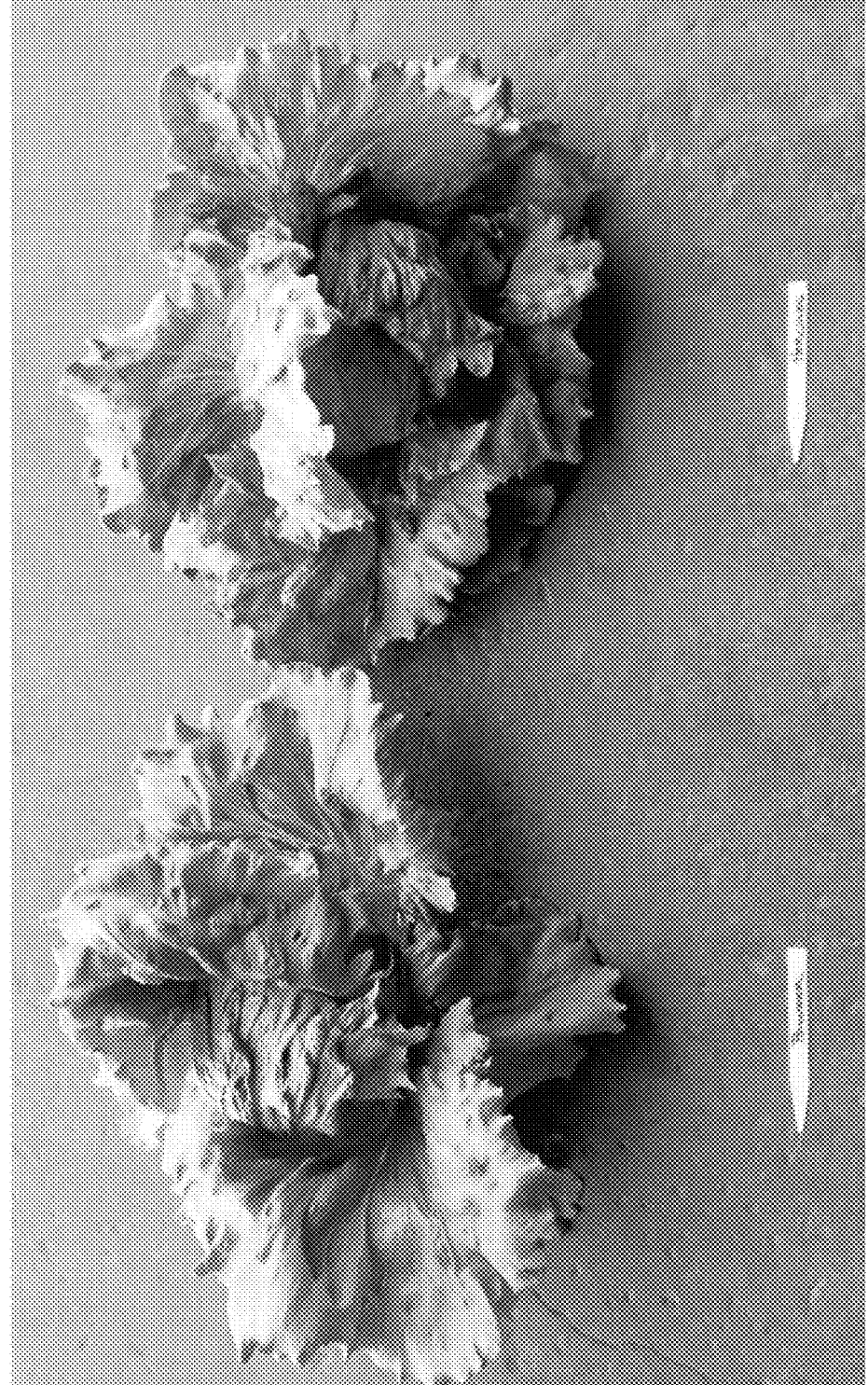
Figure 2B:
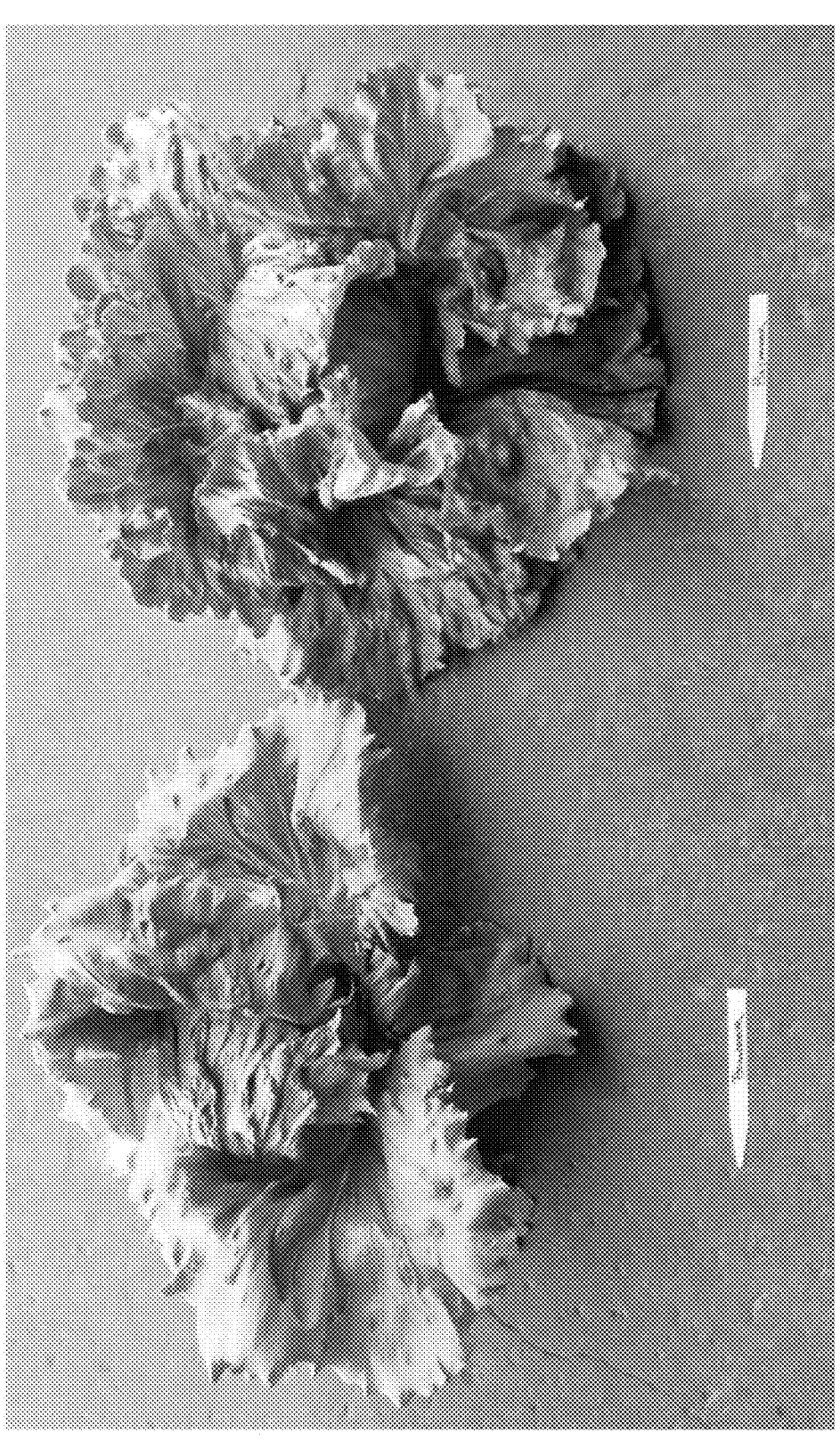
Figure 2C:
Figure 2D:
Figure 2E:
Figure 2F:
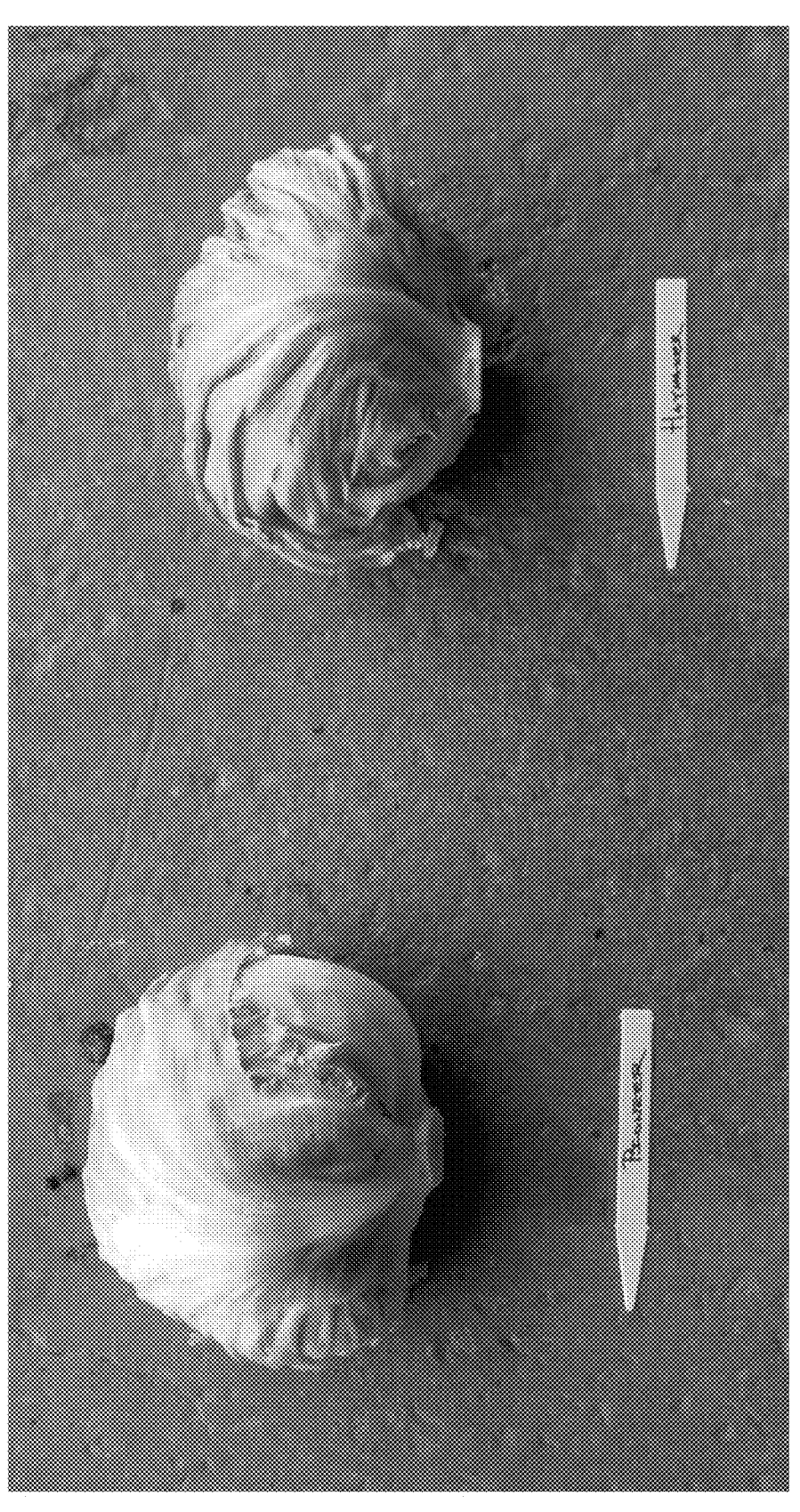
Figure 2G:
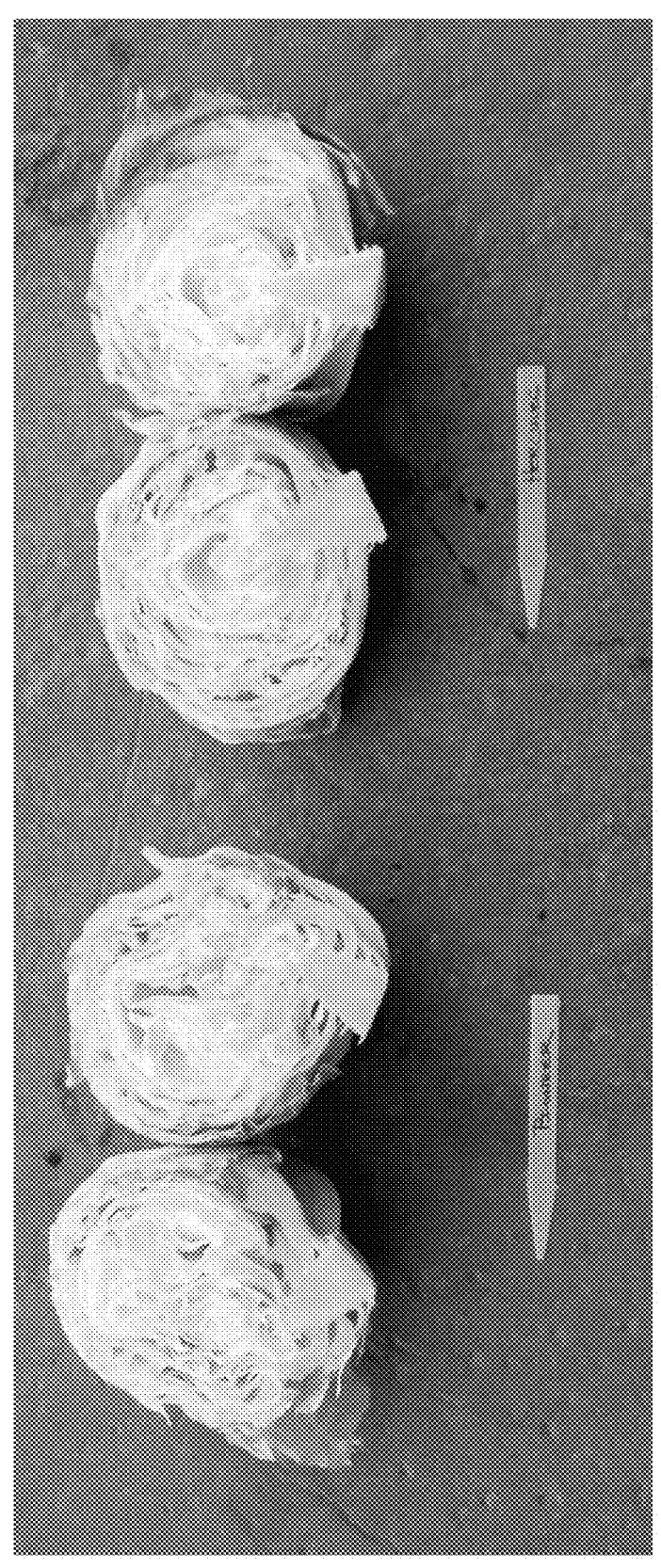
Figure 2H:
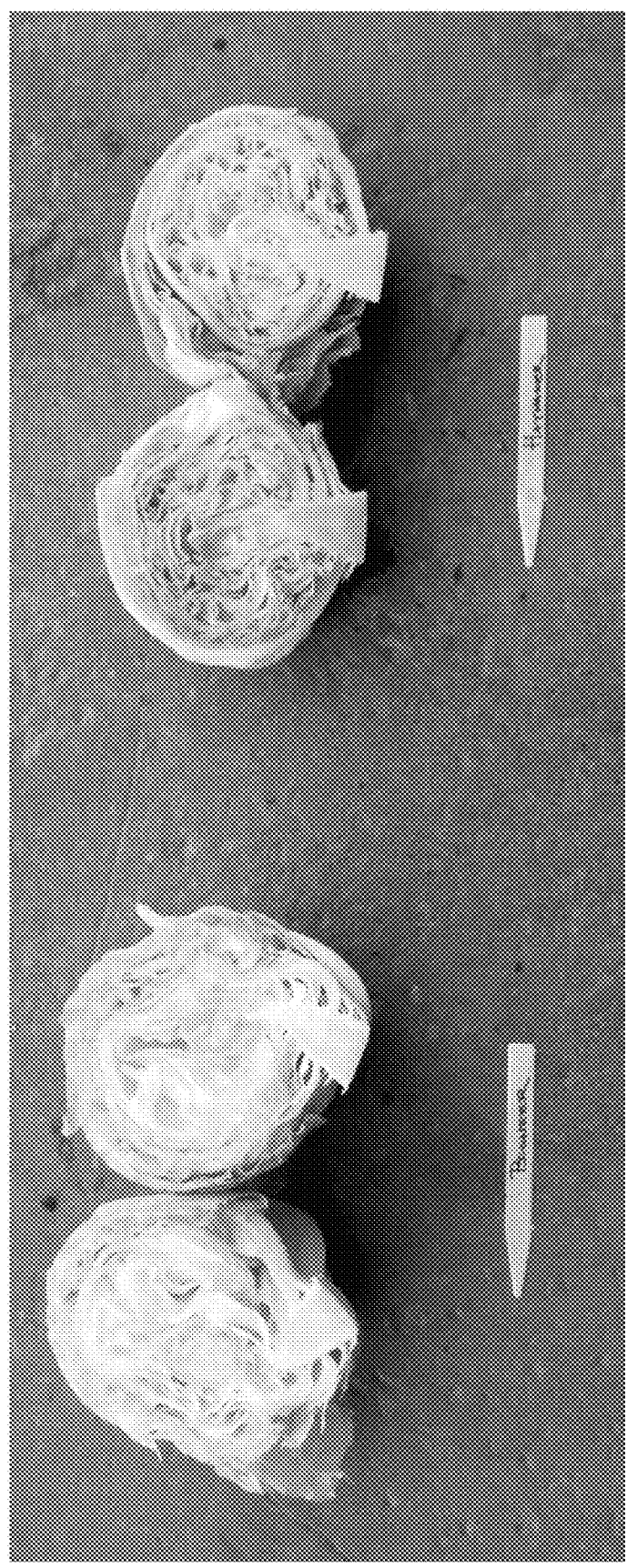
Figure 2I:
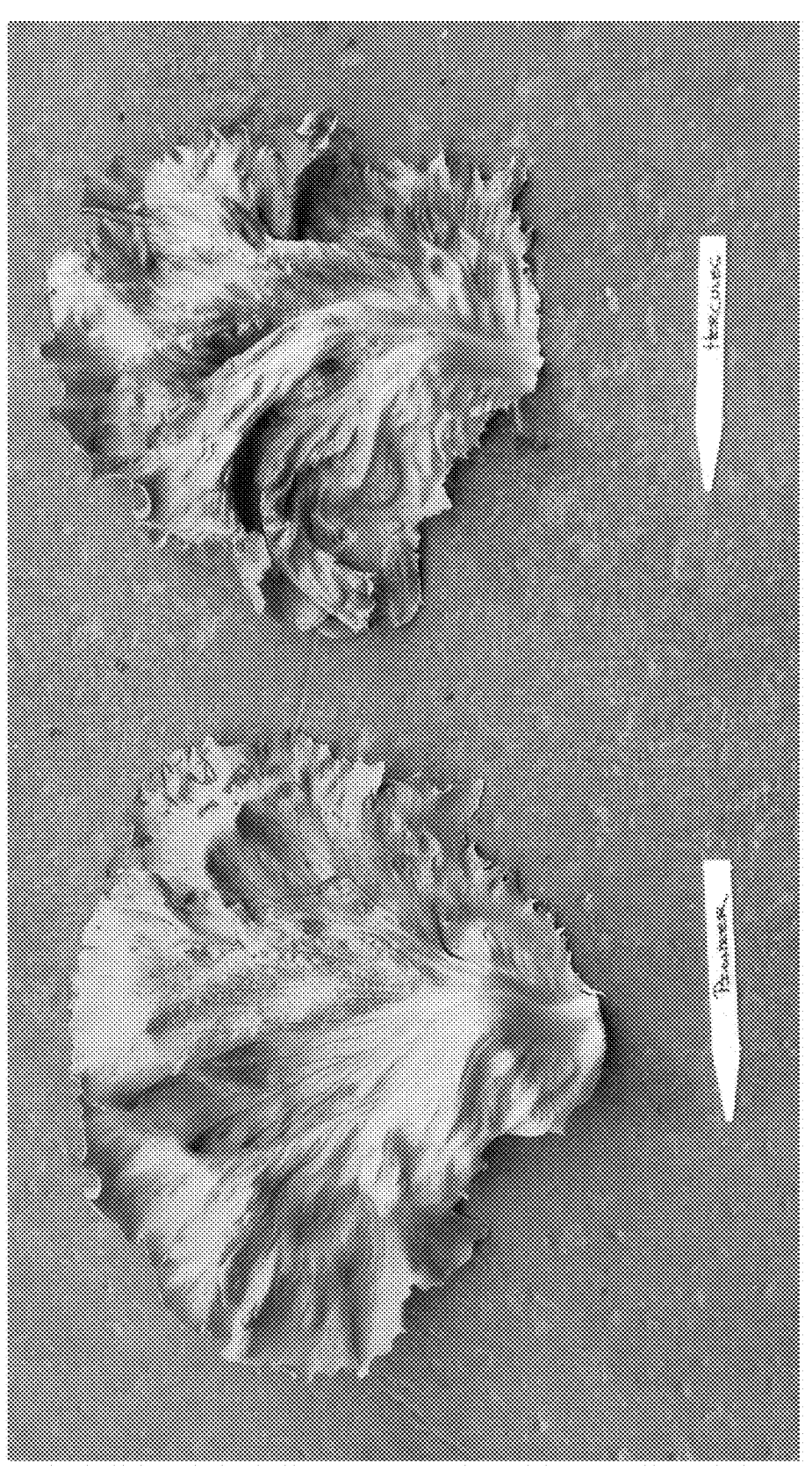
Figure 2J:
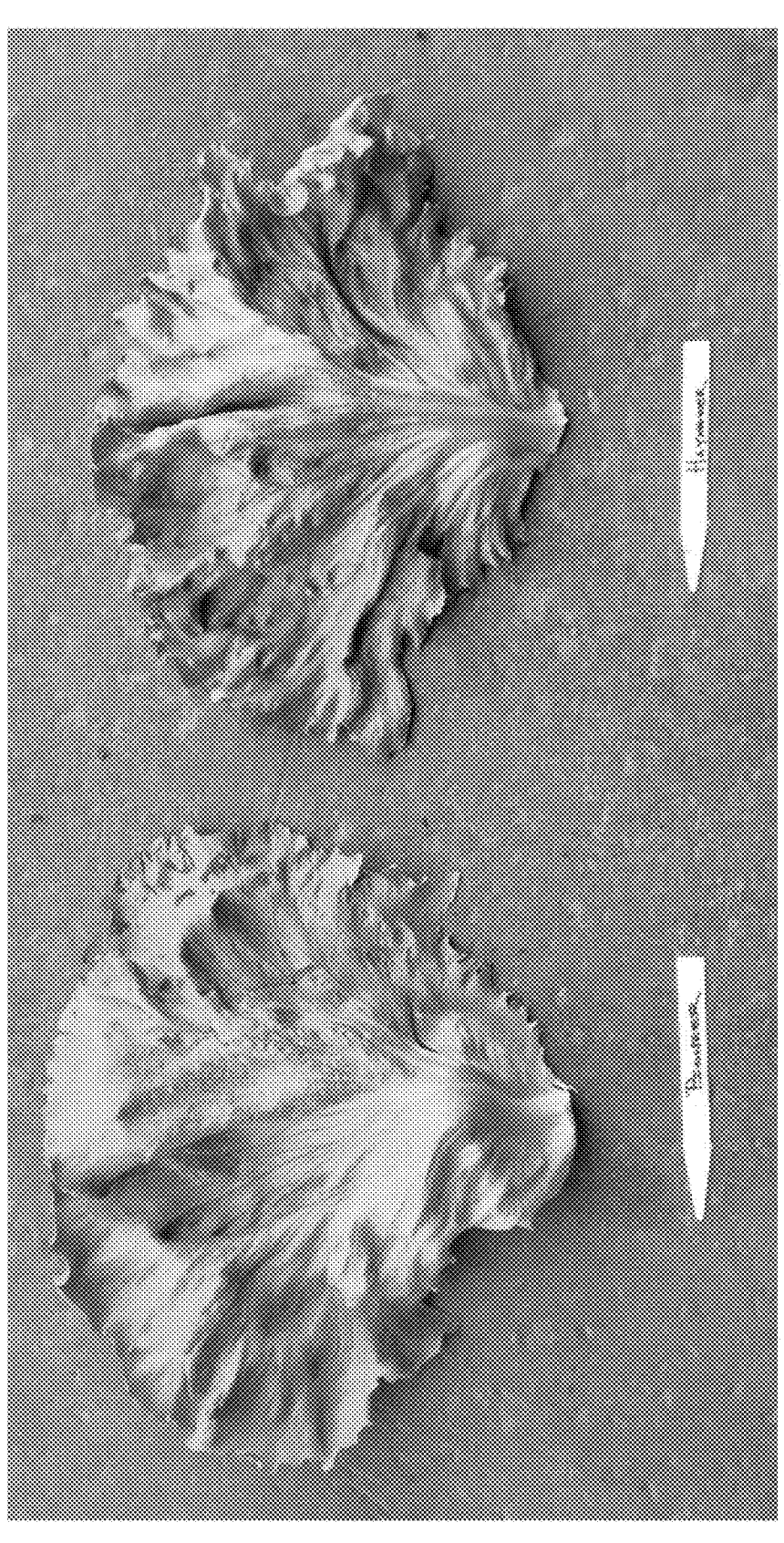
Figure 2M:
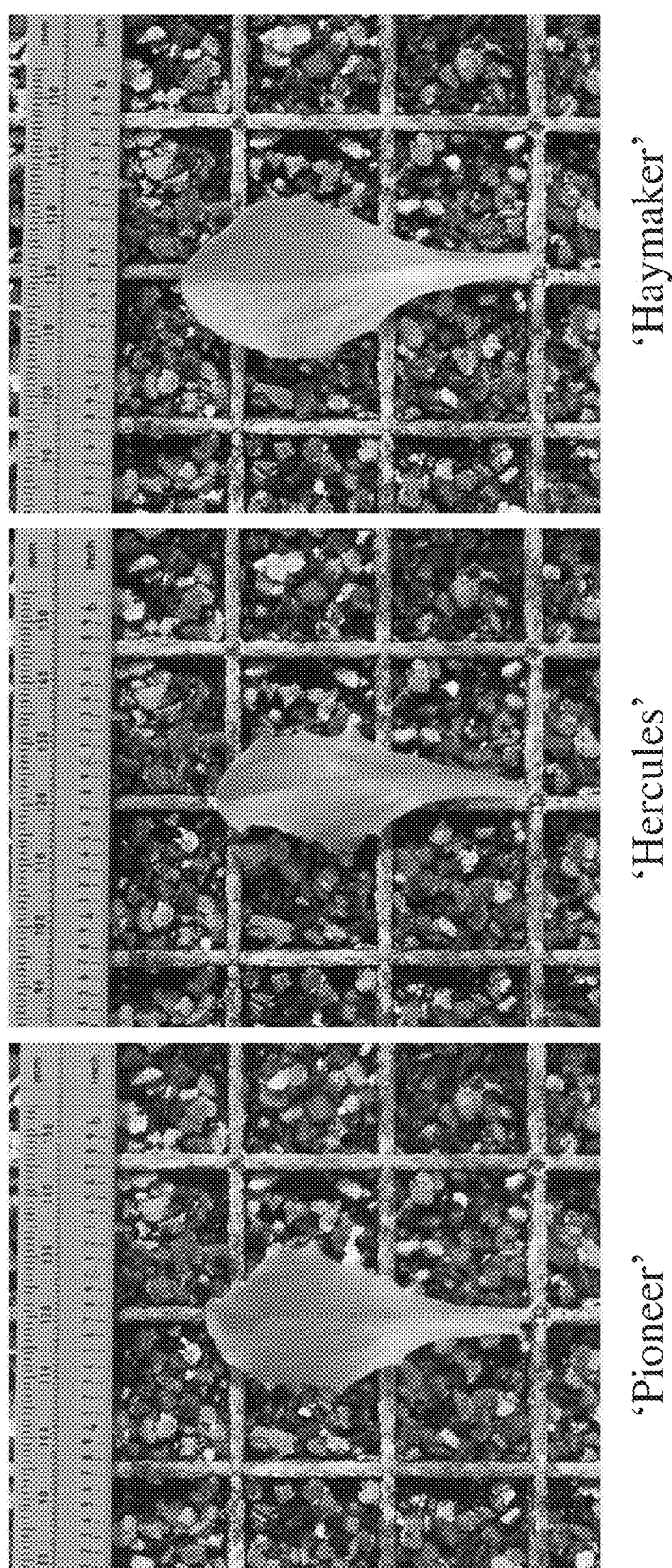

FIGS. 2A-2M show comparisons between lettuce varieties 'Pioneer', 'Hercules' (U.S. Pat. No. 10,631,491), and 'Haymaker' (U.S. Pat. No. 10,123,502). Lettuce variety 'Pioneer' is labeled as 'Pioneer' in the comparisons. FIG. 2A shows a top view of heads of lettuce varieties 'Pioneer' (left) and 'Hercules' (right). FIG. 2B shows a top view of heads of lettuce varieties 'Pioneer' (left) and 'Haymaker' (right). FIG. 2C shows a bottom view of heads of lettuce varieties 'Pioneer' (left) and 'Hercules' (right). FIG. 2D shows a bottom view of heads of lettuce varieties 'Pioneer' (left) and 'Haymaker' (right). FIG. 2E shows a side view of heads of lettuce varieties 'Pioneer' (left) and 'Hercules' (right). FIG. 2F shows a side view of heads of lettuce varieties 'Pioneer' (left) and 'Haymaker' (right). FIG. 2G shows a cross-sectional view of heads of lettuce varieties 'Pioneer' (left) and 'Hercules' (right). FIG. 2H shows a cross-sectional view of heads of lettuce varieties 'Pioneer' (left) and 'Haymaker' (right). FIG. 2I shows mature leaves of lettuce varieties 'Pioneer' (left) and 'Hercules' (right). FIG. 2J shows mature leaves of lettuce varieties 'Pioneer' (left) and 'Haymaker' (right). FIG. 2K shows plants, including stalks, of lettuce varieties 'Pioneer' (left), 'Hercules' (center), and 'Haymaker' (right) after bolting. FIG. 2L shows seedlings of lettuce varieties 'Pioneer' (left), 'Hercules' (center), and 'Haymaker' (right). FIG. 2M shows fourth leaves of lettuce varieties 'Pioneer' (left), 'Hercules' (center), and 'Haymaker' (right).

DETAILED DESCRIPTION

Definitions

In order to more clearly understand the invention, the following definitions are provided:

Big Vein virus: Big vein is a disease of lettuce caused by Lettuce Mirafiori Big Vein Virus, which is transmitted by the fungus *Olpidium virulentus*, with vein clearing and leaf shrinkage resulting in plants of poor quality and reduced marketable value.

Core Diameter: Core diameter is the diameter of the lettuce stem at the base of the cut head.

Core Length: Core length is the length of the vertically sliced lettuce plant as measured from the base of the head to the top of the apex (growing point). Core length may also be referred to as "core height."

Downy Mildew: Downy mildew is a disease caused by *Bremia lactucae*, an oomycete, characterized by leaf yellowing, whitish mold-like growth on the surface of the leaves, and eventual leaf browning and death.

Frame Diameter: The frame diameter is a measurement taken from the outer most leaf tip horizontally to the outer most leaf tip across the top of the lettuce plant at its widest point.

*Fusarium* Wilt: *Fusarium* wilt of lettuce is a disease caused by the fungus *Fusarium oxysporum* f. sp. *lactucae* that causes infected seedlings to wilt, and turn red or brown in color in inner tissues, and causes leaves of infected older plants to turn yellow and develop tip burn.

Head Diameter: Head diameter is the diameter of the vertically sliced lettuce plant head at its widest horizontal point, perpendicular to the stem.

*Impatiens* Necrotic Spot Virus (INSV): INSV is a virus of the order Bunyavirales that infects lettuce plants and causes yellowing and dead spots on leaves and stunted growth.

Lettuce Aphid (*Nasonovia ribisnigri*): Lettuce aphid is a pest that colonizes the innermost leaves of the lettuce plant, contaminating areas that cannot be treated easily with insecticides.

Lettuce Mosaic Virus: A disease that can cause a stunted, deformed, or mottled pattern in young lettuce and yellow, twisted, and deformed leaves in older lettuce.

Munsell: Munsell refers to the Munsell Color Chart, which uses the Munsell color system.

Plant Diameter: The plant diameter is a measurement across the top of the lettuce plant at its widest point. Plant diameter is an equivalent measurement to frame diameter.

Tip burn: Means a browning of the edges or tips of lettuce leaves that is a physiological response to a lack of calcium.

Taking into account these definitions, the present invention is directed to seeds of the lettuce varieties 'Big Shot' and 'Pioneer', plants produced by growing 'Big Shot' and/or 'Pioneer' lettuce seeds, heads isolated or harvested from the plants, one or more plants selected from a collection of 'Big Shot' and/or 'Pioneer' plants and seeds derived or produced therefrom; and plants produced by crossing a lettuce plant with a 'Big Shot' and/or 'Pioneer' lettuce plant and seeds derived or produced therefrom.

Objective Description of the Variety 'Big Shot'

'Big Shot' is an iceberg lettuce variety. This variety is distinct and unique to all other iceberg lettuce varieties due to its increased resistance to *Fusarium* Wilt Race 1, improved uniformity, increased head weight, and shorter core height. 'Big Shot' has a growing season that includes summer in West Coast regions of the United States, as well as fall in regions in the Southwestern United states, and is suitable for growing in the open. Lettuce variety 'Big Shot' is the result of numerous generations of plant selections chosen for its resistance to *Fusarium* Wilt Race 1.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety 'Big Shot'.

Lettuce variety 'Big Shot' has the following morphologic and other characteristics:

Plant type: Crisp (i.e., iceberg)
Seed:
Color: White
Seed light dormancy: Light not required
Heat dormancy: Susceptible
Cotyledon to fourth leaf stage:
Shape of cotyledons: Intermediate
Cotyledon length: 21.8 mm
Cotyledon width: 9.75 mm
Cotyledon index (length/width×10): 22.4
Shape of fourth leaf: Elongated Fourth leaf length: 60.6 mm
Fourth leaf width: 21.7 mm
Fourth leaf index (length/width×10): 27.9
Apical margin: Entire
Basal margin: Finely dentate
Green color: Dark green
Anthocyanin distribution: Absent
Cupping: Slight
Reflexing: None
    Mature leaves:
Incision depth: Moderate
Indentation: Deeply dentate
Undulation of apical margin: Strong
Green color: Dark green (5GY 5/8)
Anthocyanin distribution: Absent
Leaf glossiness: Glossy
Blistering: Moderate
Leaf thickness: Intermediate
Trichomes: Absent (smooth)
    Plant:
Spread of frame leaves: 47.2 cm
Head diameter: 13.9 cm
Head shape: Spherical
Head size class: Medium
Head firmness: Firm
    Butt:
Butt shape: Rounded
Midrib: Moderately raised
    Core:
Core diameter: 31.7 mm
Ratio of head diameter/core diameter:4.4
Core height from base of head to apex: 29.8 mm
    Bolting:
Number of days from first water to seed stalk emergence
under summer conditions: 72
Bolting class: Slow
Mature seed stalk height: 91.7 cm
Mature seed stalk spread: 30.7 cm
Bolter leaves: Curved
Margin: Dentate
    Bolter habit:
    Terminal inflorescence: Present
    Lateral shoots: Present
    Basal side shoots: Absent
    Disease Resistance:
*Fusarium* Wilt (*Fusarium oxysporum* f. sp. *lactucae*) Race
1: Highly resistant
Big Vein Virus: Susceptible
Lettuce Mosaic Virus: Susceptible
Downy Mildew (*Bremia lactucae*): Susceptible
Lettuce Aphid (*Nasonovia ribisnigri* 0): Susceptible
*Impatiens* necrotic spot virus (INSV): Susceptible
    Responses to stresses:
Tip burn: High resistance
Heat: Moderately resistant
Cold: Susceptible
Pink rib: Moderately resistant

Comparisons to Other Lettuce Varieties

Table 1 below compares characteristics of lettuce variety
'Big Shot' with the lettuce variety 'Hotshot' (U.S. Pat. No.
11,369,070) and 'Crusader' (PVP Certificate No. 9800351).
Column 1 lists the characteristics, column 2 shows the
characteristics for lettuce variety 'Big Shot', column 3
shows the characteristics for lettuce variety 'Hotshot', and
column 4 shows the characteristics for lettuce variety 'Crusader'. As shown in Table 1, lettuce variety 'Big Shot' has
a larger head diameter than lettuce variety 'Hotshot'.

TABLE 1

| Characteristic | 'Big Shot' | 'Hotshot' | 'Crusader' |
|---|---|---|---|
| Resistance to Fusarium Wilt Race 1 | Highly resistant | Intermediate resistance | Susceptible |
| Head diameter | 13.9 cm | 13.8 cm | 14.2 cm |
| Frame diameter | 47.2 cm | 47.4 cm | 47.3 cm |
| Head weight | 550.5 g | 543.6 g | 559.9 g |
| Core diameter | 31.7 mm | 31.3 mm | 31.6 mm |
| Core length | 29.8 mm | 30.8 mm | 32.4 mm |
| Ratio of head diameter/core diameter | 4.4 | 4.4 | 4.5 |
| Mature seed stalk height | 91.7 cm | 91.4 cm | 96.5 cm |
| Mature seed stalk spread | 30.7 cm | 34.1 cm | 30.7 cm |
| Mature Leaf Color (Munsell) | 5GY 5/8 | 5GY 5/8 | 5GY 5/6 |

Tables 2A-2C below show the results of a first field trial
which compares the head weight, head diameter, core
length, core diameter, and frame diameter of 20 plants of the
lettuce variety 'Big Shot' (Table 2A) with those of 20 plants
of lettuce variety 'Hotshot' (Table 2B) and 20 plants of
lettuce variety 'Crusader' (Table 2C).

TABLE 2A

| 'Big Shot' | Head Wt. | Head Diameter | Core Length | Core Diameter | Frame Diameter |
|---|---|---|---|---|---|
| Max | 925 g | 16.1 cm | 59 mm | 41 mm | 54.8 cm |
| Min | 465 g | 12.5 cm | 25 mm | 32 mm | 44.8 cm |
| Average | 706 g | 14.26 cm | 30.95 mm | 36.6 mm | 50.27 cm |
| Std. Dev. | 117.90 | 1.00 | 7.27 | 2.28 | 3.23 |

TABLE 2B

| 'Hotshot' | Head Wt. | Head Diameter | Core Length | Core Diameter | Frame Diameter |
|---|---|---|---|---|---|
| Max | 1000 g | 17.1 cm | 62 mm | 42 mm | 56.9 cm |
| Min | 570 g | 12.1 cm | 25 mm | 32 mm | 44.3 cm |
| Average | 728.75 g | 14.06 cm | 35.05 mm | 36.3 mm | 50.405 cm |
| Std. Dev. | 127.86 | 1.02 | 8.36 | 2.72 | 2.67 |

TABLE 2C

| 'Crusader' | Head Wt. | Head Diameter | Core Length | Core Diameter | Frame Diameter |
|---|---|---|---|---|---|
| Max | 1030 g | 17.3 cm | 52 mm | 41 mm | 55.1 cm |
| Min | 440 g | 12.4 cm | 25 mm | 32 mm | 44.6 cm |
| Average | 746 g | 14.205 cm | 34 mm | 36.3 mm | 51.02 cm |
| Std. Dev. | 137.36 | 1.31 | 7.05 | 2.34 | 2.73 |

Tables 3A-3C below show the results of a second field
trial which compares the head weight, head diameter, core
length, core diameter, and frame diameter of 20 plants of the
lettuce variety 'Big Shot' (Table 3A) with those of 20 plants
of lettuce variety 'Hotshot' (Table 3B) and 20 plants of
lettuce variety 'Crusader' (Table 3C).

TABLE 3A

| 'Big Shot' | Head Wt. | Head Diameter | Core Length | Core Diameter | Frame Diameter |
|---|---|---|---|---|---|
| Max | 896 g | 14.2 cm | 30 mm | 40 mm | 52.4 cm |
| Min | 426 g | 11.3 cm | 17 mm | 30 mm | 42.3 cm |
| Average | 658.05 g | 12.945 cm | 22.75 mm | 35.3 mm | 46.585 cm |
| Std. Dev. | 119.24 | 0.73 | 3.63 | 3.06 | 2.78 |

TABLE 3B

| 'Hotshot' | Head Wt. | Head Diameter | Core Length | Core Diameter | Frame Diameter |
|---|---|---|---|---|---|
| Max | 750 g | 15.1 cm | 25 mm | 37 mm | 50.2 cm |
| Min | 406 g | 10.9 cm | 17 mm | 29 mm | 42.4 cm |
| Average | 567.6 g | 12.595 cm | 21.2 mm | 33.45 mm | 47.185 cm |
| Std. Dev. | 96.93 | 0.94 | 2.63 | 2.48 | 2.06 |

TABLE 3C

| 'Crusader' | Head Wt. | Head Diameter | Core Length | Core Diameter | Frame Diameter |
|---|---|---|---|---|---|
| Max | 848 g | 14.5 cm | 31 mm | 40 mm | 50.3 cm |
| Min | 520 g | 12.1 cm | 21 mm | 30 mm | 45.6 cm |
| Average | 647.6 g | 12.955 cm | 24.25 mm | 34.7 mm | 48.035 cm |
| Std. Dev. | 92.14 | 0.69 | 2.65 | 2.77 | 1.52 |

Tables 4A-4C below show the results of a third field trial which compares the head weight, head diameter, core length, core diameter, and frame diameter of 20 plants of the lettuce variety 'Big Shot' (Table 4A) with those of 20 plants of lettuce variety 'Hotshot' (Table 5B) and 20 plants of lettuce variety 'Crusader' (Table 4C).

TABLE 4A

| 'Big Shot' | Head Wt. | Head Diameter | Core Length | Core Diameter | Frame Diameter |
|---|---|---|---|---|---|
| Max | 505 g | 15.2 cm | 43 mm | 31 mm | 59.8 cm |
| Min | 370 g | 12.6 cm | 26 mm | 25 mm | 41.2 cm |
| Average | 441 g | 14.015 cm | 34.5 mm | 27.8 mm | 48.925 cm |
| Std. Dev. | 46.39 | 0.70 | 4.07 | 1.58 | 4.87 |

TABLE 4B

| 'Hotshot' | Head Wt. | Head Diameter | Core Length | Core Diameter | Frame Diameter |
|---|---|---|---|---|---|
| Max | 560 g | 15.1 cm | 39 mm | 31 mm | 55.6 cm |
| Min | 350 g | 11.4 cm | 25 mm | 25 mm | 41.2 cm |
| Average | 458.5 g | 13.415 cm | 33.05 mm | 26.9 mm | 47.04 cm |
| Std. Dev. | 62.89 | 0.994868412 | 3.78 | 1.77 | 4.05 |

TABLE 4C

| 'Crusader' | Head Wt. | Head Diameter | Core Length | Core Diameter | Frame Diameter |
|---|---|---|---|---|---|
| Max | 525 g | 15.3 cm | 49 mm | 31 mm | 52.6 cm |
| Min | 320 g | 12.7 cm | 27 mm | 25 mm | 41.2 cm |
| Average | 426 g | 14.26 cm | 37 mm | 27.05 mm | 46.55 cm |
| Std. Dev. | 58.43 | 0.84 | 6.15 | 1.43 | 3.62 |

Tables 5A-5C below show the results of a fourth field trial which compares the head weight, head diameter, core length, core diameter, and frame diameter of 20 plants of the lettuce variety 'Big Shot' (Table 5A) with those of 20 plants of lettuce variety 'Hotshot' (Table 5B) and 20 plants of lettuce variety 'Crusader' (Table 5C).

TABLE 5A

| 'Big Shot' | Head Wt. | Head Diameter | Core Length | Core Diameter | Frame Diameter |
|---|---|---|---|---|---|
| Max | 575 g | 16.1 cm | 36 mm | 30 mm | 49.1 cm |
| Min | 295 g | 12.8 cm | 27 mm | 24 mm | 38.6 cm |
| Average | 396.75 g | 14.525 cm | 30.8 mm | 27 mm | 42.87 cm |
| Std. Dev. | 82.19 | 0.78 | 2.95 | 1.78 | 3.52 |

TABLE 5B

| 'Hotshot' | Head Wt. | Head Diameter | Core Length | Core Diameter | Frame Diameter |
|---|---|---|---|---|---|
| Max | 610 g | 17.3 cm | 46 mm | 34 mm | 49.8 cm |
| Min | 290 g | 13.1 cm | 27 mm | 25 mm | 39.8 cm |
| Average | 419.5 g | 14.995 cm | 33.95 mm | 28.55 mm | 45.035 cm |
| Std. Dev. | 87.81 | 1.35 | 5.40 | 2.37 | 3.20 |

TABLE 5C

| 'Crusader' | Head Wt. | Head Diameter | Core Length | Core Diameter | Frame Diameter |
|---|---|---|---|---|---|
| Max | 660 g | 17.2 cm | 48 mm | 32 mm | 49.6 cm |
| Min | 265 g | 14.1 cm | 24 mm | 25 mm | 38.6 cm |
| Average | 420 g | 15.285 cm | 34.45 mm | 28.25 mm | 43.655 cm |
| Std. Dev. | 97.59 | 0.94 | 6.91 | 2.02 | 3.59 |

Tables 6A-6B below show the results of a greenhouse trial which compares the cotyledon size (Table 6A) and fourth leaf size (Table 6B) of 20 plants of the lettuce variety 'Big Shot' with those of 20 plants of lettuce variety 'Hotshot' and 20 plants of lettuce variety 'Crusader'. Cotyledon measurements were taken from 10 day old plants, and fourth leaf measurements were taken from 18 day old plants.

TABLE 6A

| Cotyledon | 'Big Shot' | | 'Hotshot' | | 'Crusader' | |
|---|---|---|---|---|---|---|
| Leaf | Width | Length | Width | Length | Width | Length |
| Max | 11 mm | 25 mm | 11 mm | 26 mm | 12 mm | 24 mm |
| Min | 8 mm | 18 mm | 7 mm | 18 mm | 9 mm | 15 mm |
| Average | 9.75 mm | 21.8 mm | 9.3 mm | 22.3 mm | 9.95 mm | 20.3 mm |
| Std Dev | 0.91 | 1.96 | 0.98 | 2.36 | 0.76 | 2.20 |

TABLE 6B

| Fourth | 'Big Shot' | | 'Hotshot' | | 'Crusader' | |
|---|---|---|---|---|---|---|
| Leaf | Width | Length | Width | Length | Width | Length |
| Max | 28 mm | 70 mm | 76 mm | 72 mm | 31 mm | 72 mm |
| Min | 15 mm | 52 mm | 15 mm | 53 mm | 16 mm | 52 mm |
| Average | 21.7 mm | 60.6 mm | 23.45 mm | 63.75 mm | 22.55 mm | 60.3 mm |
| Std Dev | 4.39 | 5.29 | 12.88 | 4.66 | 4.47 | 4.66 |

Table 7 below shows the results of a summer field trial which compares the stalk length and frame diameter of 20 plants of the lettuce variety 'Big Shot' with those of 20 plants of lettuce variety 'Hotshot' and 20 plants of lettuce variety 'Crusader'.

TABLE 7

| | 'Big Shot' | | 'Hotshot' | | 'Crusader' | |
|---|---|---|---|---|---|---|
| | Stalk height | Frame diameter | Stalk height | Frame diameter | Stalk height | Frame diameter |
| Max | 96.3 cm | 32.3 cm | 97.3 cm | 36.1 cm | 99.4 cm | 35.1 cm |
| Min | 86.3 cm | 29.3 mc | 86.3 cm | 33.1 cm | 89.4 cm | 29.3 cm |
| Average | 91.73 cm | 30.725 cm | 91.355 cm | 34.06 cm | 96.53 cm | 30.665 cm |
| Std Dev | 2.50 | 0.99 | 3.15 | 0.74 | 2.60 | 1.30 |

Further distinguishing features are apparent from the comparison of the variety 'Big Shot' and the varieties 'Hotshot' and 'Crusader' depicted in FIGS. 1A-1M.

Objective Description of the Variety 'Pioneer'

'Pioneer' is an iceberg lettuce variety. This variety is distinct and unique to all other iceberg lettuce varieties due to its resistance to *Fusarium* Wilt Race 1, intermediate resistance to *Impatiens* Necrotic Spot Virus (INSV), improved head diameter and weight, larger frame length, and smaller core height. 'Pioneer' has a growing season that includes summer in West Coast regions of the United States and is suitable for growing in the open. Lettuce variety 'Pioneer' is the result of numerous generations of plant selections chosen for its resistance to *Fusarium* Wilt Race 1 and intermediate resistance to INSV. Specifically, variety 'Pioneer' is the result of crossing parent varieties 'Black Belt' (PVP Certificate No. 200800308) and 'Hercules' (U.S. Pat. No. 10,631,491). 'Black Belt' may also be referred to as '4 HOGS-A5-5-G2'. Neither parent line is a backcross progeny or locus converted line of a publicly disclosed line. The development of 'Pioneer' was achieved through a pedigree breeding method; in particular, filial generations 1 and 2 were grown in San Joaquin, CA, filial generation 3 was grown in San Juan Bautista, CA, filial generation 4 was grown in Paicines, CA, filial generation 5 was grown in Hollister, CA and filial generation 6 was grown in San Joaquin, CA. Variety 'Pioneer' was chosen in filial generation 6.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety 'Pioneer'.

Lettuce variety 'Pioneer' has the following morphologic and other characteristics:

Plant type: Crisp (i.e., iceberg)

Seed:

Color: White

Seed light dormancy: Light not required

Heat dormancy: Susceptible

Cotyledon to fourth leaf stage:

Shape of cotyledons: Intermediate

Cotyledon length: 19.5 mm

Cotyledon width: 8.4 mm

Cotyledon index (length/width×10): 23.2

Shape of fourth leaf: Oval

Fourth leaf length: 39.75 mm

Fourth leaf width: 18.7 mm

Fourth leaf index (length/width×10): 21.2

Apical margin: Finely dentate

Basal margin: Finely dentate

Green color: Dark green

11

Anthocyanin distribution: Absent
Cupping: Slight
Reflexing: None
   Mature leaves:
Incision depth: Moderate
Indentation: Crenate
Undulation of apical margin: Moderate
Green color: Dark green (Munsell 5GY 5/8)
Anthocyanin distribution: Absent
Leaf glossiness: Moderate
Blistering: Absent/slight
Leaf thickness: Intermediate
Trichomes: Absent (smooth)
   Plant:
Spread of frame leaves: 52.8 cm
Head diameter: 15.3 cm
Head shape: Spherical
Head size class: Medium
Head firmness: Firm
   Butt:
Butt shape: Rounded
Midrib: Flattened
   Core:
Core diameter: 33.3 mm
Ratio of head diameter/core diameter:4.6
Core height from base of head to apex: 51.6
   Bolting:
Number of days from first water to seed stalk emergence under summer conditions: 65
Bolting class: Medium
Mature seed stalk height: 104 cm
Mature seed stalk spread: 36.8 cm
Bolter leaves: Straight
Margin: Dentate
Bolter habit:
   Terminal inflorescence: Present
   Lateral shoots: Absent
   Basal side shoots: Absent
   Disease Resistance:
*Fusarium* Wilt (*Fusarium oxysporum* f. sp. *lactucae*) Race 1: Resistant
*Impatiens* Necrotic Spot Virus (INSV): Resistant
   Responses to stress
Tipburn: Intermediate Resistance

Comparisons to Other Lettuce Varieties

Table 8 below compares characteristics of lettuce variety 'Pioneer' with the lettuce variety 'Haymaker' (U.S. Pat. No. 10,123,502) and 'Hercules' (U.S. Pat. No. 10,631,491). Column 1 lists the characteristics, column 2 shows the characteristics for lettuce variety 'Pioneer', column 3 shows the characteristics for lettuce variety 'Haymaker', and column 4 shows the characteristics for lettuce variety 'Hercules'.

12

TABLE 8

| Characteristic | 'Pioneer' | 'Haymaker' | 'Hercules' |
| --- | --- | --- | --- |
| Core length | 51.6 mm | 51.6 mm | 56.9 mm |
| Frame length | 52.8 cm | 50.3 cm | 50.6 cm |
| Head weight | 710.3 g | 713.8 g | 678.6 g |
| Head diameter | 15.3 cm | 14.4 cm | 14.3 cm |
| Core diameter | 33.3 mm | 33.8 mm | 33.6 mm |
| Ratio of head diameter/core diameter | 4.6 | 4.3 | 4.3 |
| Mature seed stalk height | 104 cm | 94.7 cm | 94.7 cm |
| Mature seed stalk spread | 36.8 cm | 30 cm | 34.7 cm |
| Color (Munsell) | 5GY 5/8 | 5GY 5/8 | 5GY 5/6 |

Tables 9A-9C below show the results of a first field trial which compares the head weight, head diameter, core length, core diameter, and frame diameter of 20 plants of the lettuce variety 'Pioneer' (Table 9A) with those of 20 plants of lettuce variety 'Hercules' (Table 9B) and 20 plants of lettuce variety 'Haymaker' (Table 9C).

TABLE 9A

| 'Pioneer' | Head Wt. | Head Diameter | Core Length | Core Diameter | Frame Diameter |
| --- | --- | --- | --- | --- | --- |
| Max | 830 g | 18.1 cm | 79 mm | 37 mm | 61.2 cm |
| Min | 420 g | 13.3 cm | 42 mm | 30 mm | 48.9 cm |
| Average | 616.5 g | 15.58 cm | 60.45 mm | 33.8 mm | 53.39 cm |
| Std. Dev. | 94.05 | 1.17 | 9.07 | 1.85 | 3.50 |

TABLE 9B

| 'Hercules' | Head Wt. | Head Diameter | Core Length | Core Diameter | Frame Diameter |
| --- | --- | --- | --- | --- | --- |
| Max | 730 g | 16.2 cm | 89 mm | 36 mm | 56.4 cm |
| Min | 350 g | 12.6 cm | 51 mm | 28 mm | 37.6 cm |
| Average | 535.75 g | 14.615 cm | 66.15 mm | 32.5 mm | 49.03 cm |
| Std. Dev. | 107.47 | 0.94 | 10.78 | 2.16 | 3.87 |

TABLE 9C

| 'Haymaker' | Head Wt. | Head Diameter | Core Length | Core Diameter | Frame Diameter |
| --- | --- | --- | --- | --- | --- |
| Max | 905 g | 16.4 cm | 93 mm | 38 mm | 55.6 cm |
| Min | 515 g | 14.3 cm | 48 mm | 32 mm | 45.6 cm |
| Average | 678.5 g | 15.44 cm | 67.45 mm | 35.05 mm | 50.855 cm |
| Std. Dev. | 120.80 | 0.62 | 9.58 | 1.76 | 2.48 |

Tables 10A-10C below show the results of a first field trial which compares the head weight, head diameter, core length, core diameter, and frame diameter of 20 plants of the lettuce variety 'Pioneer' (Table 10A) with those of 20 plants of lettuce variety 'Hercules' (Table 10B) and 20 plants of lettuce variety 'Haymaker' (Table 10C).

TABLE 10A

| 'Pioneer' | Head Wt. | Head Diameter | Core Length | Core Diameter | Frame Diameter |
|---|---|---|---|---|---|
| Max | 1059 g | 18.2 cm | 60 mm | 37 mm | 60.2 cm |
| Min | 687 g | 14.1 cm | 40 mm | 27 mm | 46.1 cm |
| Average | 880 g | 15.955 cm | 48 mm | 33.3 mm | 53.535 cm |
| Std. Dev. | 110.40 | 1.03 | 5.20 | 2.41 | 3.15 |

TABLE 10B

| 'Hercules' | Head Wt. | Head Diameter | Core Length | Core Diameter | Frame Diameter |
|---|---|---|---|---|---|
| Max | 1150 g | 17.7 cm | 71 mm | 40 mm | 58.4 cm |
| Min | 670 g | 13.2 cm | 42 mm | 29 mm | 48.2 cm |
| Average | 861.75 g | 15.015 cm | 52.7 mm | 34 mm | 53 cm |
| Std. Dev. | 129.68 | 1.07 | 7.00 | 2.87 | 2.42 |

TABLE 10C

| 'Haymaker' | Head Wt. | Head Diameter | Core Length | Core Diameter | Frame Diameter |
|---|---|---|---|---|---|
| Max | 1062 g | 16.3 cm | 56 mm | 45 mm | 58.4 cm |
| Min | 687 g | 12.7 cm | 36 mm | 31 mm | 46.1 cm |
| Average | 856.45 g | 14.365 cm | 46.4 mm | 34.45 mm | 50.68 cm |
| Std. Dev. | 98.37 | 0.90 | 5.00 | 3.12 | 3.38 |

Tables 11A-11C below show the results of a first field trial which compares the head weight, head diameter, core length, core diameter, and frame diameter of 20 plants of the lettuce variety 'Pioneer' (Table 11A) with those of 20 plants of lettuce variety 'Hercules' (Table 11B) and 20 plants of lettuce variety 'Haymaker' (Table 11C).

TABLE 11A

| 'Pioneer' | Head Wt. | Head Diameter | Core Length | Core Diameter | Frame Diameter |
|---|---|---|---|---|---|
| Max | 885 g | 17.1 cm | 51 mm | 39 mm | 60.2 cm |
| Min | 530 g | 12.9 cm | 41 mm | 31 mm | 46.1 cm |
| Average | 661.25 g | 14.875 cm | 45.65 mm | 33.75 mm | 53.205 cm |
| Std. Dev. | 86.74 | 0.94 | 3.08 | 2.15 | 3.24 |

TABLE 11B

| 'Hercules' | Head Wt. | Head Diameter | Core Length | Core Diameter | Frame Diameter |
|---|---|---|---|---|---|
| Max | 895 g | 15.7 cm | 61 mm | 38 mm | 58.4 cm |
| Min | 455 g | 12.6 cm | 41 mm | 31 mm | 48.9 cm |
| Average | 664 g | 14.1 cm | 51.95 mm | 34.85 mm | 53.2 cm |
| Std. Dev. | 119.36 | 0.96 | 5.28 | 1.87 | 2.19 |

TABLE 11C

| 'Hay-maker' | Head Wt. | Head Diameter | Core Length | Core Diameter | Frame Diameter |
|---|---|---|---|---|---|
| Max | 840 g | 15.1 cm | 49 mm | 37 mm | 58.4 cm |
| Min | 445 g | 12.4 cm | 35 mm | 31 mm | 46.7 cm |
| Average | 658.75 g | 13.56 cm | 42.55 mm | 33.45 mm | 50.94 cm |
| Std. Dev. | 100.73 | 0.82 | 4.41 | 1.76 | 3.20 |

Tables 12A-12C below show the results of a first field trial which compares the head weight, head diameter, core length, core diameter, and frame diameter of 20 plants of the lettuce variety 'Pioneer' (Table 12A) with those of 20 plants of lettuce variety 'Hercules' (Table 12B) and 20 plants of lettuce variety 'Haymaker' (Table 12C).

TABLE 12A

| 'Pioneer' | Head Wt. | Head Diameter | Core Length | Core Diameter | Frame Diameter |
|---|---|---|---|---|---|
| Max | 835 g | 16.7 cm | 67 mm | 36 mm | 57.6 cm |
| Min | 475 g | 13.6 cm | 44 mm | 28 mm | 44.4 cm |
| Average | 683.25 g | 14.73 cm | 52.25 mm | 32.2 mm | 51.095 cm |
| Std. Dev. | 93.78 | 0.75 | 6.70 | 2.28 | 4.12 |

TABLE 12B

| 'Hercules' | Head Wt. | Head Diameter | Core Length | Core Diameter | Frame Diameter |
|---|---|---|---|---|---|
| Max | 849 g | 15.4 cm | 84 mm | 36 mm | 53.2 cm |
| Min | 437 g | 12.6 cm | 35 mm | 30 mm | 42.1 cm |
| Average | 652.9 g | 13.64 cm | 57.15 mm | 32.85 mm | 47.265 cm |
| Std. Dev. | 97.45 | 0.76 | 10.23 | 2.01 | 3.15 |

TABLE 12C

| 'Haymaker' | Head Wt. | Head Diameter | Core Length | Core Diameter | Frame Diameter |
|---|---|---|---|---|---|
| Max | 998 g | 15.7 cm | 65 mm | 36 mm | 55.1 cm |
| Min | 424 g | 12.1 cm | 33 mm | 28 mm | 44.3 cm |
| Average | 661.3 g | 14.1 cm | 49.95 mm | 32.2 mm | 48.815 cm |
| Std. Dev. | 157.35 | 1.14 | 7.75 | 2.31 | 2.94 |

Tables 13A-13B below show the results of a greenhouse trial which compares the cotyledon size (Table 13A) and fourth leaf size (Table 13B) of 20 plants of the lettuce variety 'Pioneer' with those of 20 plants of lettuce variety 'Hercules' and 20 plants of lettuce variety 'Haymaker'. Cotyledon measurements were taken from 10 day old plants, and fourth leaf measurements were taken from 18 day old plants.

TABLE 13A

| Cotyledon | 'Pioneer' | | 'Hercules' | | 'Haymaker' | |
|---|---|---|---|---|---|---|
| Leaf | Width | Length | Width | Length | Width | Length |
| Max | 10 mm | 24 mm | 9 mm | 25 mm | 10 mm | 21 mm |
| Min | 5 mm | 15 mm | 7 mm | 15 mm | 8 mm | 14 mm |
| Average | 8.4 mm | 19.5 mm | 7.95 mm | 20.25 mm | 9.15 mm | 18.85 mm |
| Std Dev | 1.31 | 2.19 | 0.76 | 2.81 | 0.67 | 2.03 |

TABLE 13B

| Fourth | 'Pioneer' | | 'Hercules' | | 'Haymaker' | |
|---|---|---|---|---|---|---|
| Leaf | Width | Length | Width | Length | Width | Length |
| Max | 22 mm | 50 mm | 29 mm | 69 mm | 28 mm | 70 mm |
| Min | 15 mm | 29 mm | 15 mm | 50 mm | 16 mm | 53 mm |
| Average | 18.7 mm | 39.75 mm | 21.6 mm | 59 mm | 21.35 mm | 61.5 mm |
| Std Dev | 2.20 | 7.13 | 4.20 | 4.62 | 3.84 | 5.39 |

Table 14 below shows the results of a summer field trial which compares the stalk length and frame diameter of 20 plants of the lettuce variety 'Pioneer' with those of 20 plants of lettuce variety 'Hercules' and 20 plants of lettuce variety 'Haymaker'.

TABLE 14

| | 'Pioneer' | | 'Hercules' | | 'Haymaker' | |
|---|---|---|---|---|---|---|
| | Stalk height | Frame diameter | Stalk height | Frame diameter | Stalk height | Frame diameter |
| Max | 109.2 cm | 41.2 cm | 100.3 cm | 39.1 cm | 105.6 cm | 39.3 cm |
| Min | 98.1 cm | 32.4 cm | 91.2 cm | 26.7 cm | 85.1 cm | 23.9 cm |
| Average | 104.03 cm | 36.785 cm | 94.74 cm | 34.715 cm | 94.695 cm | 30.005 cm |
| Std Dev | 2.86 | 2.65 | 2.84 | 3.67 | 5.42 | 4.95 |

Further distinguishing features are apparent from the comparison of the variety 'Pioneer' and the varieties 'Hercules' and 'Haymaker' depicted in FIGS. 2A-2M.

Further Embodiments

Breeding

In lettuce breeding, lines are selected for their appropriate characteristics. For example, one line may be selected for its size and the color of its lettuce leaves. Another line may be selected for resistance to disease. Crosses are made, for example, to produce disease resistant lettuce varieties with dark green leaves and improved size.

To optimize crossing, it is important to note that lettuce is an obligate self-pollinating species. This means that the pollen is shed before stigma emergence, assuring 100% self-fertilization. Since each lettuce flower is an aggregate of about 10-20 individual florets (typical of the Compositae family), manual removal of the anther tubes containing the pollen is performed by procedures well known in the art of lettuce breeding.

The manual removal of anther tubes, though an effective means to ensure the removal of all self-pollinating possibilities, is very tedious and time consuming when a large number of crosses are to be made. The breeders have therefore adapted a well-documented and modified method of making crosses more efficiently using these methods. This particular type of cross was made by first misting the designated male flowers to wash the pollen off prior to fertilization. This process of misting is a proven and effective means of pollen removal that assures crossing or hybridization. About 60-90 minutes past sunrise, flowers to be used for crossings are selected. The basis for selection are open flowers, with the stigma emerged and the pollen visibly attached to the single stigma (about 10-20 stigma). Using 3-4 pumps of water from a regular spray bottle, the pollen is washed off with enough pressure to dislodge the pollen grains, but not enough to damage the style. Excess water is dried off with clean paper towels. About 30 minutes later, the styles should spring back up and the two lobes of the stigma are visibly open in a "V" shape. Pollen from another variety or donor parent is then introduced by gently rubbing the stigma and style of the donor parent to the maternal parent. Tags with the pertinent information on date and pedigree are then secured to the flowers in order to keep track.

About 2-3 weeks after pollination, seeds are harvested when the involucre have matured. The seeds are eventually sown and in the presence of markers such as leaf color or leaf margins, the selfed or maternal seedlings or plants are identified. Generally, there are no visible markers and breeders must wait until the $F_2$ generations when expected segregation patterns for the genetic character of interest can be followed. This latter situation mandates a lengthy wait to determine if hybrids are produced. Two relevant references teaching methods for out crossing lettuce are: (1) Ryder, E. J. and A. S. Johnson. 1974. Mist depollination of lettuce flowers. Hortscience 9:584; and (2) Nagata, R. T. 1992. Clip and Wash Method of Emasculation for Lettuce. Hortscience 27(8):907-908 both of which are hereby incorporated by reference in their entirety for the purpose of providing details on the techniques well known in the art.

Selection

In addition to crossing, selection may be used to identify and isolate new lettuce lines. In lettuce selection, lettuce seeds are planted, the plants are grown and single plant selections are made of plants with desired characteristics. Such characteristics may include improved head and frame size, deeper or darker green leaf color, etc. Seed from the single plant selections are harvested, separated from seeds of the other plants in the field and re-planted. The plants from the selected seed are monitored to determine if they exhibit the desired characteristics of the originally selected line. Selection work is continued over multiple generations to increase the uniformity of the new line.

DEPOSIT INFORMATION

Lettuce Variety 'Pioneer'

A deposit of at least 625 seeds of the lettuce variety 'Pioneer' was made with the American Type Culture Collection (ATCC), ATCC Patent Depository, 10801 University Boulevard, Manassas, Virginia, 20110, USA, and assigned ATCC Number PTA-127991. The seeds deposited with the ATCC on Dec. 22, 2025 were obtained from the seed of the variety maintained by Pinnacle Seed, Inc., having an address of P.O. Box 222672, Carmel, California 93923, United States of America, since prior to the filing date of the application. Access to this deposit will be available during the pendency of this application to persons determined by the Commissioner of Patents and Trademarks to be entitled thereto under 37 C.F.R. § 1.14 and 35 U.S.C. § 122. Upon issuance, the Applicant will make the deposit available to the public consistent with all of the requirements of 37 C.F.R. § 1.801-1.809.

This deposit of the lettuce variety 'Pioneer' will be maintained in the ATCC, which is a public depository, for a period of 30 years, or at least 5 years after the most recent request for a sample of the deposit, or for the effective life of the patent, whichever is longer, and will be replaced if it becomes nonviable during that period. Applicant has no authority to waive any restrictions imposed by law on the transfer of biological material or its transportation in commerce. Applicant does not waive any infringement of rights granted under this patent or under the Plant Variety Protection Act (7 USC 2321 et seq.).

What is claimed:

1. A *Lactuca sativa* seed designated as 'Pioneer', representative sample of seed having been deposited under ATCC Accession Number PTA-127991.

2. A *Lactuca sativa* plant produced by growing the seed of claim 1.

3. A plant part from the plant of claim 2.

4. The plant part of claim 3, wherein said part is a head, a leaf, or a portion thereof.

5. The plant part of claim 4, wherein said part is a head.

6. A *Lactuca sativa* plant having all the physiological and morphological characteristics of the *Lactuca sativa* plant of claim 2.

7. A plant part from the plant of claim 6.

8. The plant part of claim 7, wherein said part is a head, a leaf, or a portion thereof.

9. The plant part of claim 8, wherein said part is a head.

10. An $F_1$ hybrid *Lactuca sativa* plant having 'Pioneer' as a parent where 'Pioneer' is grown from the seed of claim 1.

11. A pollen grain or an ovule of the plant of claim 2.

12. A tissue culture of the plant of claim 2.

13. A *Lactuca sativa* plant regenerated from the tissue culture of claim 12, wherein the plant has all of the morphological and physiological characteristics of a lettuce plant produced by growing seed designated as 'Pioneer', representative sample of seed having been deposited under ATCC Accession Number PTA-127991.

14. A method of making *Lactuca sativa* seeds, said method comprising crossing the plant of claim 2 with another lettuce plant and harvesting seed therefrom.

15. A method of selecting *Lactuca sativa*, comprising:

a) growing more than one plant from the seed of claim 1; and b) selecting a plant from step a).

*    *    *    *    *